US009550001B2

(12) United States Patent
Tworowska et al.

(10) Patent No.: US 9,550,001 B2
(45) Date of Patent: Jan. 24, 2017

(54) COMPOSITIONS, METHODS OF SYNTHESIS AND USE OF CARBOHYDRATE TARGETED AGENTS

(75) Inventors: Izabela Tworowska, Houston, TX (US); Jennifer Sims-Mourtada, Bellaire, TX (US); Ebrahim S. Delpassand, Houston, TX (US)

(73) Assignee: RadioMedix Inc., Houston, TX (US)

( * ) Notice: Subject to any disclaimer, the term of this patent is extended or adjusted under 35 U.S.C. 154(b) by 179 days.

(21) Appl. No.: 14/128,347

(22) PCT Filed: Jun. 20, 2012

(86) PCT No.: PCT/US2012/043255
§ 371 (c)(1),
(2), (4) Date: Apr. 7, 2014

(87) PCT Pub. No.: WO2012/177701
PCT Pub. Date: Dec. 27, 2012

(65) Prior Publication Data
US 2014/0228551 A1    Aug. 14, 2014

Related U.S. Application Data

(60) Provisional application No. 61/498,950, filed on Jun. 20, 2011.

(51) Int. Cl.
| A61K 51/04 | (2006.01) |
| C07H 17/07 | (2006.01) |
| C07H 13/04 | (2006.01) |
| C07H 23/00 | (2006.01) |
| C07H 15/26 | (2006.01) |
| C07H 17/04 | (2006.01) |

(52) U.S. Cl.
CPC ....... *A61K 51/0472* (2013.01); *A61K 51/0491* (2013.01); *A61K 51/0497* (2013.01); *C07H 13/04* (2013.01); *C07H 15/26* (2013.01); *C07H 17/04* (2013.01); *C07H 17/07* (2013.01); *C07H 23/00* (2013.01); *A61K 51/0482* (2013.01)

(58) Field of Classification Search
CPC .................................................. A61K 51/0482
See application file for complete search history.

(56) References Cited

U.S. PATENT DOCUMENTS

| 4,141,654 A | 2/1979 | Wardlaw et al. |
| 4,988,496 A | 1/1991 | Srinivasan et al. |
| 5,175,343 A | 12/1992 | Fritzberg et al. |
| 5,242,679 A | 9/1993 | Fritzberg et al. |
| 5,364,613 A | 11/1994 | Sieving et al. |
| 5,605,672 A | 2/1997 | Bogdanov et al. |
| 5,648,063 A | 7/1997 | Gries et al. |
| 5,652,361 A | 7/1997 | Simon et al. |
| 5,707,605 A | 1/1998 | Meade et al. |
| 5,880,281 A | 3/1999 | Argese et al. |
| 5,980,862 A | 11/1999 | Meade et al. |
| 6,071,490 A | 6/2000 | Griffiths et al. |
| 6,265,483 B1 * | 7/2001 | Guilard ............. B01D 53/1493 428/404 |
| 6,565,828 B2 | 5/2003 | Liu |
| 6,613,305 B1 | 9/2003 | Collins et al. |
| 6,673,333 B1 | 1/2004 | Meade et al. |
| 6,692,724 B1 | 2/2004 | Yang et al. |
| 6,713,045 B1 | 3/2004 | Meade et al. |
| 6,737,247 B2 | 5/2004 | Bogdanov et al. |
| 6,770,261 B2 | 8/2004 | Meade et al. |
| 7,138,104 B2 | 11/2006 | Carpenter, Jr. |
| 7,354,568 B1 | 4/2008 | Meade et al. |
| 7,586,102 B2 | 9/2009 | Mourtada et al. |
| 2002/0076379 A1 | 6/2002 | Platzek et al. |
| 2003/0053954 A1 | 3/2003 | Meade et al. |
| 2004/0170563 A1 | 9/2004 | Meade et al. |
| 2005/0002866 A1 | 1/2005 | Meade et al. |
| 2005/0232866 A1 | 10/2005 | Melchior et al. |
| 2006/0051291 A1 | 3/2006 | Adam et al. |
| 2006/0142207 A1 | 6/2006 | Tidmarsh et al. |

(Continued)

FOREIGN PATENT DOCUMENTS

| CA | 2361115 | 7/2000 |
| WO | 2006121889 | 11/2006 |

(Continued)

OTHER PUBLICATIONS

Altava et al. (Ind. Eng. Chem. Res. 2000, 39, 3589-3595).*
Guillier et al. (Chem. Rev. 2000, 100, 2091-2157).*
Canadian Office Action dated Feb. 11, 2015 for counterpart Canadian Application No. 2,843,313, 4 pages.
Response to Canadian Office Action dated Feb. 11, 2015 filed Aug. 11, 2015 for counterpart Canadian Application No. 2,843,313, 19 pages.
International Search Report in corresponding International Patent Application No. PCT/US2012/0433255 dated Jan. 31, 2013 (5 pages).
Written Opinion of the International Searching Authority in corresponding International Patent Application No. PCT/US2012/043255 dated Jan. 31, 2013 (3 pages).

(Continued)

*Primary Examiner* — Michael G Hartley
*Assistant Examiner* — Melissa Perreira
(74) *Attorney, Agent, or Firm* — JL Salazar Law Firm

(57) ABSTRACT

The invention provides D02S derivatives conjugated to monosaccharide ligands directly or through a linker and optionally chelated to a metal, wherein the D02S derivatives having the following structure: wherein $R_1'$, $R_2'$ are each independently —OH or —O-alkyl; $R_1$ is a hydrogen, a linker, or a ligand; $R_3$ is a linker and/or a ligand; and n is an integer from 1 to 10; the linker is an amino acid, a peptide, an amino alcohol, a polyethyllylene glycol, an alkyl, an alkenyl, an alkynyl, an azide, an aromatic compound, a carboxylic acid, or an ester, the alkyl, alkenyl, or alkynyl is optionally substituted with an alkyl, a halogen, a nitro group, a hydroxyl group, an amino group, or a carboxyl group; the ligand is a GLUT1 targeting moiety.

8 Claims, 30 Drawing Sheets

(56) References Cited

U.S. PATENT DOCUMENTS

| | | |
|---|---|---|
| 2006/0182687 A1 | 8/2006 | Yang et al. |
| 2007/0048216 A1 | 3/2007 | Norenberg |
| 2007/0248537 A1 | 10/2007 | Yang et al. |
| 2007/0297976 A1 | 12/2007 | Yang et al. |
| 2008/0089842 A1 | 4/2008 | Pagel et al. |
| 2009/0087377 A1 | 4/2009 | Azhdarinia et al. |
| 2010/0008856 A1 | 1/2010 | Wright et al. |
| 2012/0207684 A1 | 8/2012 | Basilion et al. |
| 2014/0228551 A1 | 8/2014 | Tworowska et al. |
| 2014/0271482 A1 | 9/2014 | Low et al. |
| 2014/0275533 A1 | 9/2014 | Kularatne et al. |
| 2014/0378677 A1 | 12/2014 | Moore |

FOREIGN PATENT DOCUMENTS

| | | |
|---|---|---|
| WO | 2008-119036 A2 | 10/2008 |
| WO | 2009054327 | 4/2009 |
| WO | 2009-108868 A2 | 9/2009 |

OTHER PUBLICATIONS

International Preliminary Report on Patentability in corresponding International Patent Application No. PCT/US2012/043255 dated Dec. 23, 2013 (4 pages).

European Search Report for Patent Application No. 12803364.4-2721045 dated Oct. 28, 2014, 1 page.

European Search Report for Patent Application No. 12803364.4-2721045 dated Oct. 10, 2014, 9 pages.

Jean-Philippe Bapst et al: "Glycosylated DOTA-[alpha]-Melanocyte-Stimulating Hormone Analogues for Melanoma Targeting: Influence of the Site of Glycosylation on in Vivo Biodistribution", XP05514860, Bioconjugate Chemistry, vol. 20, No. 5, May 20, 2009, 10 pages.

Examination Search Report for Canadian Patent Application No. 2,843,313 dated Nov. 17, 2015, 3 pages.

Parry, David M. and Pedersen, Peter L., "Intracellular Localization and Properties of Particulate Hexokinase in the Novikoff Ascites Tumor", The Journal of Biological Chemistry, vol. 258, No. 18, (1983), pp. 10904-10912.

Thorens, Bernard and Mueckler, Mike, "Glucose transporters in the 21st Century", Am J Physiol Endocrinol Metab, vol. 298(2010), pp. E141-E145.

Weihua, Zhang et al., "Survival of Cancer Cells is Maintained by EGFR Independent of Its Kinase Activity", Cancer Cell, vol. 13(2008), pp. 385-393.

Gottschaldt, Michael et al., "In111 and Ga111 Complexes of Sugar-Substituted Tripodal Trisalicylidene Imines: The First 68Ga-Labelled Sugar Dervative", Eur. J. Inorg. Chem., 2009, pp. 4298-4307.

Bormans, Guy M. et al., "Synthesis and Biologic Evaluation of 11C-Methyl-D-Glucoside, a Tracer of the Sodium-Dependent Glucose Transporters", The Journal of Nuclear Medicine, vol. 44, No. 7(2003), pp. 1075-1081.

Panwar, Puja et al., "Radiolabeling and Biological Evaluation of DOTA-Ph-Al Derivative Conjugated to Anti-EGFR Antibody ior egf/r3 for Targeted Tumor Imaging and Therapy", Cancer Biology & Therapy, vol. 4, No. 8(2005), pp. 854-860.

Helmke, Burkhard M. et al., "Expression of SGLT-1 in preneoplastic and neoplastic lesions of the head and neck", Oral Oncology, vol. 40 (2004), pp. 28-35.

Ishikawa, Nobuhisa et al., "SGLT Gene Expression in Primary Lung Cancers and Their Metastatic Lesions", Japanese Journal Cancer Research, vol. 92 (2001), pp. 874-879.

Green, David E. et al., "Carbohydrate-Bearing 3-Hydroxy-4-puridinonato Complexes of Gallium(III) and Indium(III)", Bioconjugate Chemistry, vol. 16 (2005), pp. 1597-1609.

Chen, Yue et al., "Noninvasive Scintigraphic Detection of Tumor with 99mTc-DTPA-Deoxyglucose: An Experimental Study", Cancer Biotherapy & Radiopharmaceuticals, vol. 22, No. 3 (2007), pp. 403-405.

European Application No. 12803364.4 Office Action dated Feb. 22, 2016, 5 pages.

Warburg, Otto, "On the Origin of Cancer Cells", Science, vol. 123, No. 3191(1956), pp. 309-314.

Al-Nahhas et al., "What can gallium-68 PET add to receptor and molecular imaging?", Eur J Nucl Med Mol Imaging, Dec. 2007, 1897-1901, vol. 34(12).

Boswell et al., "Optimization of labeling and metabolite analysis of copper-64-labeled azamacrocyclic chelators by radio-LC-MS", Nucl Med Biol., Jan. 2005, 29-38, vol. 32(1).

Chappell et al., "Synthesis and evaluation of novel bifunctional chelating agents based on 1,4,7, 10-tetraazacyclododecane-N,N',N'N'-tertraacetic acid for radiolabeling proteins", Nucl Med Biol., Aug. 2003, 581-95, vol. 30(6).

Engelhardt et al., "The Synthesis and Radiolabeling of 2-Nitroimidazole Derivatives of Cyclam and Their Preclinical E.pdf," J Mucl. Med., 2002, 837-850, vol. 43.

Froidevaux et al., Int J. Cancer, 2002, vol. 98, pp. 930-937.

English translation of Mexican Office Action dated Oct. 29, 2015 for counterpart Mexican Application No. MX/a/2009/010412, 3 pages.

Schillaci, O. et al., "Fusion Imaging in Nuclear Medicine—Applications of Dual-Modality Systems in Oncology", Cancer Biother. Radiopharm., vol. 19, pp. 1-10 (2004)., 10 pages.

Gambhir, S. S. et al., "Imaging Transgene Expression With Radionuclide Imaging Technologies", Neoplasia, vol. 2, Nos. 1-2, Jan.-Apr. 2000, pp. 118-138., 21 pages.

Tjuvajev, Juri Gelovani et al., "Comparison of Radiolabeled Nucleoside Probes (FIAU, FHBG, and FHPG) for PET Imaging of HSV1-tk Gene Expression", The Journal of Nuclear Medicine, vol. 43, No. 8, Aug. 2002, pp. 1072-1083., 13 pages.

Reed, John C., "Apoptosis-targeted therapies for cancer", Cancer Cell, vol. 3, Jan. 2003, pp. 17-22., 6 pages.

Yaghoubi, Shahriar et al., "Human Pharmacokinetic and Dosimetry Studies of [18F]FHBG: A Reporter Probe for Imaging Herpes Simplex Virus Typw-1 Thymidine Kinase Reporter Gene Expression", The Journal of Nuclear Medicine, vol. 42, No. 8, Aug. 2001, pp. 1225-1234., 11 pages.

Ye, Yunpeng et al., "Polyvalent Carbocyanine Molecular Beacons for Molecular Recognitions", J. Am., Chem. Soc., vol. 126, 2004, pp. 7740-7741., 2 pages.

Mason, N. Scott et al., "Positron Emission Tomography Radiochemistry", Neuroimag. Clin. N. Am., vol. 13 (2003), pp. 671-687., 17 pages.

Srivastava, Suresh C., "Is There Life After Technetium: What is the Potential for Developing New Broad-Based Radionuclides?", Seminars in Nuclear Medicine, vol. XXVI, No. 2 Apr. 1996, pp. 119-131., 13 pages.

Alauddin, Mian M., et al. "Synthesis of 9-[(3-[18 F]-fluoro-1-hydroxy-2-propoxy) methyl] guanine ([18 9-FHPG): A potential imaging agent of viral infection and gene therapy using PET." Nuclear medicine and biology 23.6 (1996): 787-792., 6 pages.

Alauddin, Mian M., et al. "Evaluation of 9-[(3-18 F-fluoro-1-hydroxy-2-propoxy) methyl] guanine ([18 F]-FHPG in vitro and in vivo as a probe for PET imaging of gene incorporation and expression in tumors." Nuclear medicine and biology 26.4 (1999): 371-376., 6 pages.

Alauddin, Mian M., and Peter S. Conti. "Synthesis and preliminary evaluation of 9-(4-[18 F]-fluoro-3-hydroxymethylbutyl) guanine ([18 F] FHBG): a new potential imaging agent for viral infection and gene therapy using PET." Nuclear medicine and biology 25.3 (1998): 175-180., 6 pages.

Connors. Tom. "Anticancer drug development: the way forward." The Oncologist 1.3 (1996): 180-181., 2 pages.

Pan, Dongfeng, et al. "Rapid synthesis of a 5'-fluorinated oligodeoxy-nucleotide: a model antisense probe for use in imaging with positron emission tomography (PET)." Bioorganic & medicinal chemistry letters 8.11 (1998): 1317-1320., 4 pages.

Gambhir, Sanjiv S., et al. "Imaging adenoviral-directed reporter gene expression in living animals with positron mission tomography." Proceedings of the National Academy of Sciences 96.5 (1999): 2333-2338., 6 pages.

Gambhir, Sanjiv S., et al. "A mutant herpes simplex virus type 1 thymidine kinase reporter gene shows improved sensitivity for

(56) References Cited

OTHER PUBLICATIONS imaging reporter gene expression with positron emission tomography." Proceedings of the National Academy of Sciences 97.6 (2000): 2785-2790., 6 pages.
Namavari, Mohammad, et al. "Synthesis of 8-[18 F] fluoroguanine derivatives: in vivo probes for imaging gene expression with positron emission tomography." Nuclear medicine and biology 27.2 (2000): 157-162., 6 pages.
Paulino, Arnold C., Wade L. Thorstad, and Timothy Fox. "Role of fusion in radiotherapy treatment planning." Seminars in nuclear medicine. vol. 33. No. 3. WB Saunders, 2003., 6 pages.
Remington's Pharmaceutical Sciences, 18th Ed., Mack Printing Company, 1990, pp. 1289-1329, 43 pages.
Proceedings of the fifty-fourth Annual Meeting, Microscopy Society of America; G. W. Bailey, J. M. Corbett, R. V. W. Dimlich, J. R. Michael and N. J., Zaluzec (Eds.). San Francisco Press, San Francisco, CA, pp. 898-899 (1996)., [online, retrieved from http://www.nanoprobes.com/applications/MSA96lip.html on Jan. 13, 2016], 3 pages.
Gatley, S. J., et al. "Radiopharmaceuticals for positron emission tomography. Development of new, innovative tracers for measuring the rates of physiologic and biochemical processes." Acta radiologica. Supplementum 374 (1989): 7-11., 6 pages.
International Preliminary Report on Patentability and Written Opinion for PCT Patent Application No. PCT/US2008/058476, dated Nov. 26, 2009, 8 pages.
Office Action for Taiwan Patent Application No. 097112535 dated Mar. 29, 2013, 12 pages.
International Search Report for European Patent Application No. EP-08732945.4 dated Nov. 15, 2012, 18 pages.
Examination Report for Australian Patent Application No. 2008230771 dated Aug. 10, 2012, 5 pages.
Office Action for Canadian Patent Application No. 2,682,064 dated May 22, 2012, 2 pages.
Office Action for Canadian Patent Application No. 2,682,064 dated May 19, 2011, 5 pages.
Moulin, C., et al., "Interaction studies between europium and a surfactant cage "TAC8" by time-resolved laser-induced fluorescence", Analytica Chimica Acta 378, (1999), Elsevier Science B.V., PII: S0003-2670(98)00644-8, pp. 47-54.
Office Action for Mexican Patent Application No. MX/a/2009/010412 dated Aug. 1, 2013, 7 pages.
Office Action for Mexican Patent Application No. MX/a/2009/010412 dated May 6, 2014, 14 pages.
Office Action and English Translation for Mexican Patent Application No. MX/a/2009/010412 dated Jan. 28, 2015, 10 pages.
International Preliminary Report on Patentability for PCT Patent Application No. PCT/US2012/043255 dated Jan. 9, 2014, 5 pages.
Smith, "Molecular imaging with copper-64", Journal of Inorganic Biochemistry, 2004, vol. 98, pp. 1874-1901.
International Search Report and Written Opinion for PCT Patent Application No. PCT/US2008/58476 dated Jun. 30, 2008, 6 pages.
Lukes, et al., "Complexes of tetraazacycles bearing methylphosphinic/phosphonic acid pendant arms with copper (II), zinc (II) and lanthanides (II). A comparison with their acetic acid analogues", Coordination Chemistry Reviews, Jun. 2001, vol. 216-217, pp. 287-312.
Huskens, et al., "Alkaline Earth Metal and Lanthanide (III) Complexes of Ligands Based upon 1, 4, 7, 10-Tetraazacyclododecane-1, 7-bis(acetic acid)", Inorg. Chem., 1997, vol. 36(7), pp. 1495-1503.
Lecci, et al., "Current concepts on imaging in radiotherapy", Eur J Nucl Med Mol Imaging., Apr. 2008, vol. 35(4), pp. 821-837.
Maecke, et al., "(68)Ga-labeled peptides in tumor imaging", J Nucl Med., Jan. 2005, vol. 46(1),172S-8S.
Misra, et al., "Biological and Clinical Aspects of Lanthanide Coordination Compounds", Bioinorg Chem Appl., 2004, vol. 2(3-4), pp. 155-192.
Schmid, et al., "Synthesis and evaluation of a radiometal-labeled macrocyclic chelator-derivatised thymidine analog," Nucl Med Biol., Apr. 2006, vol. 33(3), pp. 359-366.
Trokowski, et al., "Selective Sensing of Zinc Ions with a PARACEST Contrast Agent", Angew. Chem. Int. Ed., Magnetic Resonance Imaging, No. 44, 2005, pp. 6920-6923.
Gano, L., et al., "Radiolanthanide complexes with tetraazamacrocycles bearing methylphosphonate pendant arms as bone seeking agents"; The Quarterly Journal of Nuclear Medicine and Molecular Imaging, Original Articles, vol. 51, Mar. 2007, XP-002686621; pp. 6-15.
Szilagyi, Erika, et al., "Equilibria and formation kinetics of some cyclen derivative complexes of lanthanides" Inorganica Chimica Acta 298 (2000); pp. 226-234.
Cable, Morgan L., et al., "Bacterial Spore Detection by [Tb3+{macrocycle)(dipicolinate)] Luminescence"; JACS communications, Journal of the American Chemical Society, published on the Web Jan. 23, 2007; No. 129; pp. 1474-1475.
Yoo, Jeongsoo, et al., "Comparative in Vivo Behavior Studies of Cyclen-Based Copper-64 Complexes: Regioselective Synthesis, X-ray Structure, Radiochemistry, log P, and Biodistribution"; Journal of Medical Chemistry, vol. 47, 2004; pp. 6625-6637.
Dumont, Arnaud, et al., "Reg ioselective synthesis of 1 ,7 -d iprotected 1,4,7,1 O-tetraazacyclododecane and preparation of a dialcohol dicarboxylic macrocyclic ligand"; Tetrahedron Letters, vol. 35, No. 22, Elsevier Science Ltd. 1994; XP000605423; pp. 3707-3710.
Di Vaira, Massimo, et al., "Theoretical investigation on the geometries of DOTA and DOTA-like complexes and on the transition states of their conformational equilibria"; New Journal of Chemistry, vol. 26, 2002, pp. 136-144.
Albert, Rainer, et al., "Direct Synthesis of [DOTA-DPhe1]-Octreotide and [DOTA-DPhe1 ,Tyr3]-Octreotide (SMT487): Two conjugates for Systemic Delivery of Radiotherapeutical Nuclides to Somatostatin Receptor Positive Tumors in Man"; Bioorganic & Medicinal Chemistry Letters 8 (1998); pp. 1207-1210.
Velikyan, Irina, PhD., et al., "Preparation and Evaluation of 68Ga-DOTA-hEGF for Visualization of EGFR Expression in Malignant Tumors"; Journal of Nuclear Medicine, No. 46, 2005; XP-002404435; pp. 1881-1888.
Di Vai Ra, Massimo, et al., "Synthesis and co-ord ination chern istry of 1 ,7 -bis{ carboxymethyl )-4, 1 O-bis{ 1-methylimidazol-2-ylmethyl)-1 ,4,7, 10-tetraazacyclododecane"; J. Chern. Soc., Dalton Trans., published Jan. 1, 1998; pp. 1879-1884.
Kim, et al., "Cancer's Molecular Sweet Tooth and the Warburg Effect", Cancer Res, Sep. 2006, 66:18, pp. 3927-8930.
Canada Office Action dated Aug. 19, 2016 for Canada Application No. 2,843,313, 3 Pages.

\* cited by examiner

A)

B)

| Loading efficiency | | |
|---|---|---|
| COOH-donor | Time | YIELD (%) |
| Fmoc-Asn-Glc(OAc)$_4$ | 1h | 15 |
| | 24h | 79 |
| Asparagine (*lit.*) | 20min | 78 |
| DO3A tBu-ester | 1h | 21 |
| | 24h | 57 |
| Fmoc-DO3A tBu-ester | 12h | 70 | ized compounds are temporarily attached to the insoluble polymer
COMPOSITIONS, METHODS OF SYNTHESIS AND USE OF CARBOHYDRATE TARGETED AGENTS

TECHNICAL FIELD

The present invention relates to the field of radiochemistry, nuclear imaging, radionuclide therapy, drug development and chemical synthesis. More particularly, it relates to a strategy for synthesis and radiolabeling of targeted ligands.

BACKGROUND OF THE INVENTION

Increased glycolysis is a biochemical hallmark of neoplastic cells (Warburg, 1956). Overexpression of glucose transporters in the cell-membranes of cancer cells results in increased glucose uptake (Kim and Dang, 2006). Furthermore, increased activity of glycolytic enzymes, such as hexokinase, phosphorylates glucose to prohibit its exit from the cell (Parry and Pedersen, 1983). This results in increased accumulation and consumption of glucose by cancer cells. Two families of glucose transporters have been reported in humans: GLUT [Solute Carrier family 2 (facilitated glucose transporter), gene name SLC2A] and SGLT [Solute carrier family 5 (sodium/glucose cotransporter); gene name: SLC5A]. While members of the GLUT family of transporters rely on existing concentration gradients to transport glucose from one side of the membrane to the other, members of the SGLT family transport sugars inside the cell against a concentration gradient by active transport. To date, 14 members of the GLUT family have been identified (GLUT1-14) (Thorens and Mueckler). Although there is significant sequence homology among the GLUTs, they display differential expression in tissues and have varying affinities for glucose and related sugars. GLUT1; GLUT2, and GLUT5 have been shown to be overexpressed in cancer. GLUT3 is primarily expressed on neurons, while GLUT4 and GLUT12 are primarily expressed in cardiac and skeletal muscle and their presence in the cell membrane is regulated by insulin. Six members of the SGLT family have been identified (SGLT1-6). Of these, SGLT-1 and SGLT-2 are implicated in transport of sugars. Expression of SGLT-1 in normal tissues is restricted to the small intestine and renal proximal tubes, while SGLT-2 is expressed on the apical membranes of cells in the renal convoluted proximal tubules. SGLT-1 has high affinity and low capacity for glucose transport, while SGLT-2 has lower affinity and higher capacity. (Thorens and Mueckler) Increased expression of both SGLT-1 and SGLT-2 have been reported in primary and metastatic cancers (Helmke et al., 2004, Ishikawa et al., 2001, Weihua et al., 2008)

The increased accumulation of glucose in neoplastic cells has been exploited for development of diagnostic and therapeutic agents. Radiolabeled carbohydrates have been developed for nuclear imaging of cancer. The most successful of these, 2-$^{18}$F-fluoro-2-deoxyglucose (FDG) is currently the gold standard for positron emission tomography (PET). Other sugar-based PET agents have also been developed, including $^{18}$F-Fluoroacetyl-D-glucosamine (Fujiwara et al., 1990), $^{68}$Ga-2-amino-2-deoxyglucose-based 3-hydroxy-4pyridonato complexes (Green et al., 2005), $^{68}$Ga-tripodal trissalicylaldimine complexes functionalized with xylose, glucose or galactose (Gottschaldt, 2009) $^{11}$C-methyl-glucoside (US2010/0008856, Bormons et al, 2003). Radiolabeled sugars have also been developed for SPECT imaging including $^{99m}$Tc-Glucosamine-dipicolylamine, US2006/0051291) $^{99m}$Tc-tricarbonyl-N-(2'-Hydroxybenzyl)-2-amino-2-deoxy-D-glucose, (US2006/0051291) $^{99m}$Tc Ehtylenedicysteine-glucosamine (US 2007/0248537), $^{111}$In-DOTA-glucosamine, (US2006/0142207A1), $^{99m}$Tc-DTPA-deoxyglucose (Chen et al., 2007)

Solid phase approach is a robust, efficient and reproducible method of synthesis of library of compounds. It was successfully applied for the synthesis of peptides, nucleotides, and glycopeptides. In solid phase, synthesized compounds are temporary attached to the insoluble polymer resins, allowing them to be readily separated from coupling agents and by-products during elongation process. After completion of the synthesis, final compound is released from the polymer support with high yield and purity. Application of solid phase approach for the development of imaging or therapeutic agents is still limited. SPPS was used for the synthesis peptidyl imaging agents (U.S. Patent Application Publication No. 2008/0089842). Amino-functionalized chelator was immobilized on the resin and coupled to the C-terminus and/or backbone of the peptide. After cleaving from the resin, amino-chelator-peptide was labeled with lanthanide metals.

Target-specific radiopharmaceuticals consist of a tissue targeting biomolecule attached to a radionuclide. Commonly used cyclotron-produced radionuclides (i.e. $^{11}$C, $^{13}$N, $^{15}$O and $^{18}$F) may be covalently linked to targeting molecules. Alternatively, complexes consisting of a targeting ligand, bifunctional chelating agent and a radionuclide, can be used for nuclear imaging and therapy. In this case, the radionuclide, most commonly a radiometal, is stably coordinated by the bifunctional chelating agent (BFCA). Common BFCAs for radiometallic chelation include DTPA, hydrazinonicotinamide (HYNIC), mercaptoacetyltriglycine (MAG3), tetraaza compounds (i.e. 1,4,7,10-tetraazacyclododecane-1,4,7,10-tetraacetic acid [DOTA] and macrocyclic derivatives) and ethylenedicysteine (EC). Each BFCA possesses various combinations of electron-donating atoms for metal chelation. For diagnostic radiopharmaceuticals, γ-emitting radiometals such as $^{68}$Ga and $^{64}$Cu are commonly used for PET, and $^{99m}$Tc, $^{111}$In and $^{67}$Ga are commonly used for SPECT. Additionally, α-emitting ($^{225}$Ac and $^{213}$Bi) and β-emitting ($^{90}$Y, $^{177}$Lu, and $^{186/188}$Re) radiometals can be used for radionuclide therapy.

Diagnostic imaging techniques such as computed tomography (CT) and magnetic resonance imaging (MRI) provide anatomical information about disease sites. While these modalities are commonly-used for monitoring changes in tumor size, they cannot assess functional changes occurring within cells or tumors. Functional imaging modalities use radiotracers to image, map and measure biological attributes of disease, such as metabolism, proliferation and surface receptor expression. As a result, functional imaging techniques such as Positron Emission Tomography (PET) and Single Photon Emission Computed Tomography (SPECT) have been experiencing explosive growth due to advances in molecular imaging technology. New molecular imaging targets for diagnosis and therapy have been developed to visualize disease states and pathological processes without surgical exploration of the body. In particular, targeted radiopharmaceuticals offer promising capabilities for the non-invasive assessment of the pathophysiology of diseases. Schillaci, O. & Simonetti, G., Cancer Biother. Radiopharm. 19: 1-10 (2004); Paulino, et al, Semin Nucl. Med. 33: 238-43 (2003).

In contrast to traditional radiotherapy methods, radionuclide therapy utilizes active targeting for improved tumor specificity and localization of radiation in tumor cells, thereby minimizing the effects on normal tissue. This approach uses high-affinity cell binding ligands to target radioactivity to tissues expressing a particular receptor. Radiolabeled monoclonal antibodies were among the first targeted therapies developed and have shown moderate clinical success, particularly for the treatment of Non-Hodgkin's lymphoma. However, the large size, limited diffusion and slow blood clearance of the tumor-seeking antibodies have limited their clinical utility. To address these concerns, radiolabeled peptides and low/intermediate molecular weight biologically-active proteins have been employed into the design of novel radionuclide therapies (Pnwar et al., 2005). The smaller size of these molecules confers desirable pharmacokinetic properties that are favorable for therapy, such as higher target-to-background ratios and faster blood clearance.

SUMMARY OF THE INVENTION

Embodiments of the present invention relates to the field of radiochemistry, nuclear imaging, radionuclide therapy, drug development and chemical synthesis. More particularly, embodiments of the invention relate to a strategy for solid phase synthesis and radiolabeling of ligands. Embodiments of the invention further relate to methods of using those radiolabeled ligands for radionuclide therapy and tissue-specific disease imaging Embodiments of the present invention provide methods for the synthesis of DO2S compounds conjugated to targeting ligands by solid phase approach. In preferred embodiments, the targeting ligands are carbohydrates. The DO2S compounds can be conjugated directly to the targeting ligands or through linkers.

A DO2S derivative has the following general structure:

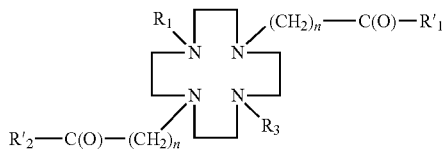

wherein $R_1'$, $R_2'$ are each a hydroxyl group, and $R_1$ is a hydrogen, a linker, or a ligand, and $R_3$ is a linker or a ligand, and n is an integer from 1 to 10, preferably from 1 to 4. The linkers may be amino acids, peptides, amino alcohols, polyethylylene glycols, alkanes, alkenes, alkynes, azide aromatic compounds, carbohydrates, carboxylic acids, esters, phosphororganic compounds, sulfonates.

In accordance with embodiments of the invention, the linker may comprise —$(CH_2)_n$—X, wherein X is a hydroxyl, an amino, or a carboxyl group, and n is an integer from 1 to 10, preferably from 1 to 4, and wherein the linker may be optionally substituted (e.g., one or more H on the alkyl chain may be replaced with an alkyl (e.g., $C_1$-$C_6$ alkyl), a halogen, a nitro group, a hydroxyl group, an amino group, or a carboxyl group).

In accordance with embodiments of the invention, the ligand may be selected from the group consisting of a carbohydrate, peptide, protein, antibody, nucleoside, nucleotide, heterocyclic compound, or alcohol. In preferred embodiments, the ligand may be carbohydrates, such as 2-deoxyglucose, 1' amino-sugar, 2' amino-sugar, 1'2'-amino-sugar, 2'-amino-methylglycoside, etc. In preferred embodiments, the ligand may be a glucose.

In preferred embodiments, the DO2S derivative has the following structure:

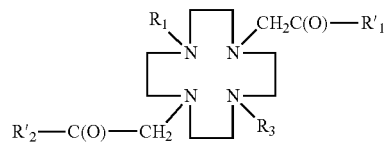

In another aspect, the disclosure relates to a composition comprising a DO2S derivative conjugated to a monosaccharide ligand directly or through a linker and optionally chelated to a metal. The DO2S has the following structure:

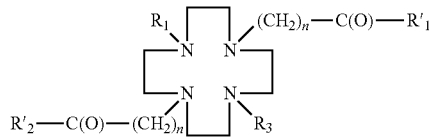

wherein $R_1'$, and $R_2'$ are each independently —OH; $R_1$, and $R_3$ comprise a ligand, optionally attached to the DO2S derivative via linker; n is 1. The linker is an amino acid, a peptide, an amino alcohol, a polyethylene glycol, an alkyl, an alkenyl, an alkynyl, an azide, an aromatic compound, a carboxylic acid, or an ester, the alkyl, alkenyl, or alkynyl is optionally substituted with an alkyl, a halogen, a nitro group, a hydroxyl group, an amino group, or a carboxyl group. The ligand is a GLUT1 targeting moiety, wherein the GLUT-1 targeting moiety is 2-deoxyglucose, a 1'2'-diaminosugar, genistein, and/or scutellarin.

Examples of DO2S derivatives may include:

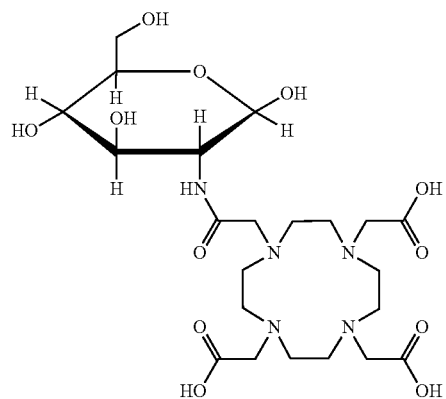

1a

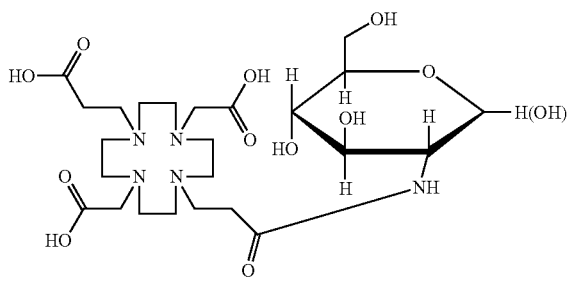

1b

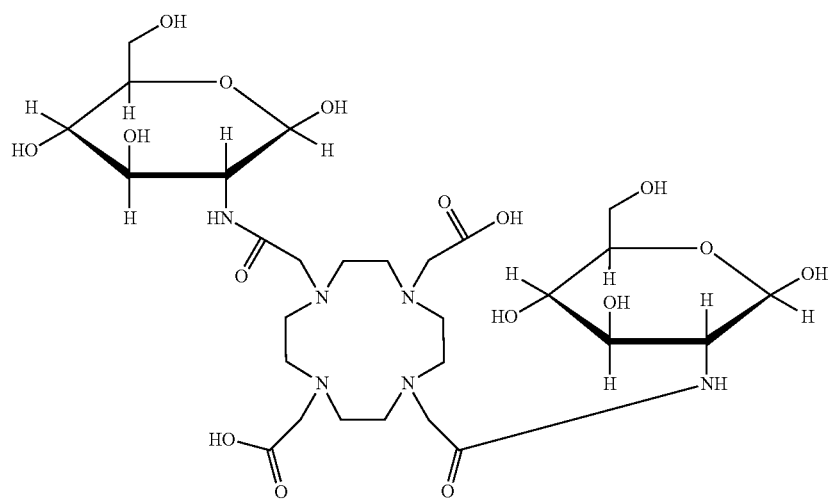
2a
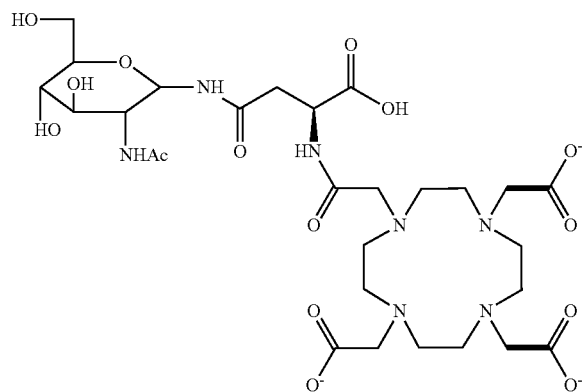
3
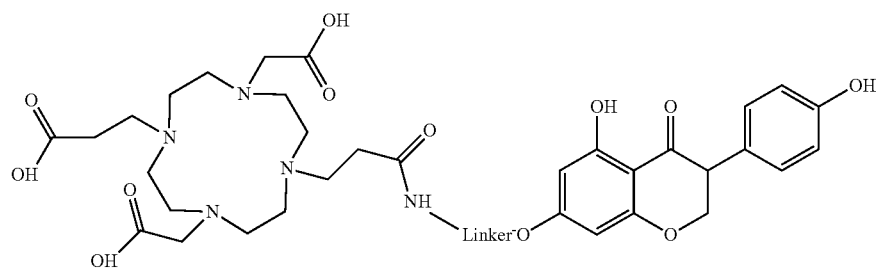
4
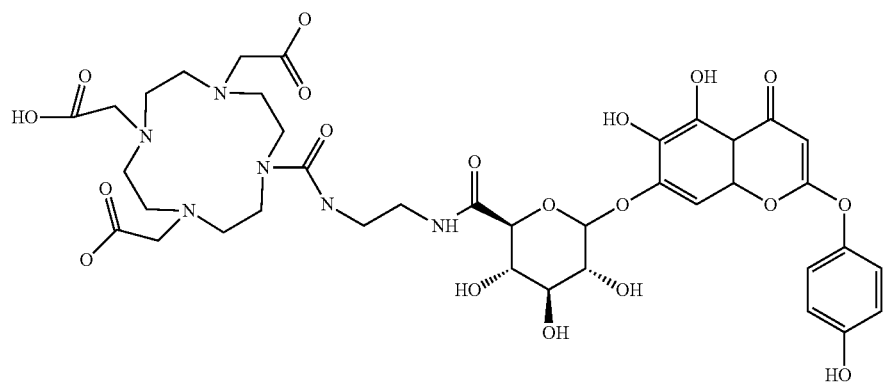

-continued

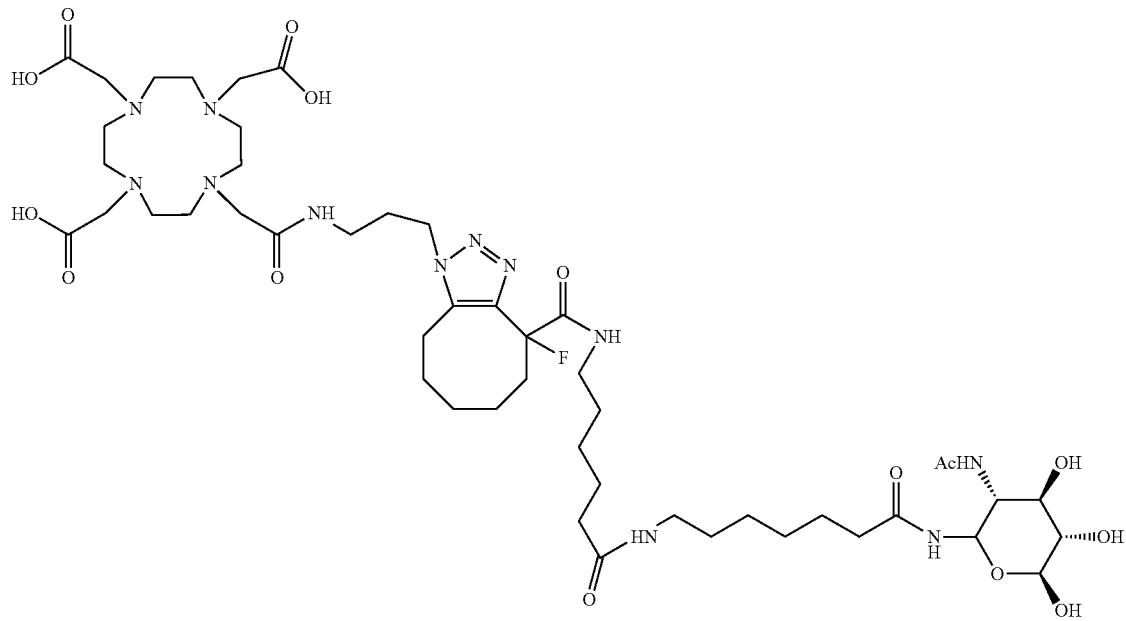

Some embodiments of the invention comprise a metal or a radionuclide chelated to the DO2S derivative. Generally, any α-emitter, β-emitter, γ-emitter, or β/γ-emitter may be used in conjunction with embodiments of the invention. Preferred α-emitters include $^{211}$At, $^{212}$Bi and $^{223}$Ra. Preferred β-emitters include $^{90}$Y and $^{225}$Ac. Preferred β/γ-emitters include $^{67}$Cu, $^{89}$Sr, $^{153}$Sm, $^{166}$Ho, $^{177}$Lu, $^{186}$Re and $^{188}$Re. Preferred γ-emitters include $^{62}$Cu, $^{64}$Cu, $^{67}$Ga, $^{68}$Ga, $^{94m}$Tc, $^{99m}$Tc and $^{111}$In.

In accordance with some embodiments of the invention, the radionuclide may be one selected from $^{45}$Ti, $^{59}$Fe, $^{60}$Cu, $^{61}$Cu, $^{62}$Cu, $^{64}$Cu, $^{67}$Cu, $^{67}$Ga, $^{68}$Ga, $^{89}$Sr, $^{90}$Y, $^{86}$Y, $^{94m}$Tc, $^{99m}$Tc, $^{111}$In, $^{149}$Pm, $^{153}$Gd, $^{153}$Sm, $^{166}$Ho, $^{177}$Lu, $^{186}$Re, $^{188}$Re, $^{211}$At, $^{212}$Bi, or $^{225}$AC. In preferred embodiments, the radionuclide is $^{68}$Ga or $^{177}$Lu.

Some embodiments of the invention provide methods of radiolabeling DO2S ligand conjugates on solid phase. In preferred embodiments, the radiometal is $^{68}$Ga or $^{177}$Lu.

In accordance with some embodiments of the invention, paramagnetic substances, such as Gd, Mn, Cu or Fe, may be used—i.e., chelated with DO2S derivatives for use in embodiments of the present invention.

Some embodiments of the invention provide methods for the treatments of medical conditions by administering to subjects compositions comprising DO2S compounds conjugated to GLUT-1 targeting ligands. The DO2S compounds may be optionally chelated to a metal species Some embodiments of the invention provide methods of diagnostic imaging performed on cellular level by application of DO2S compound conjugated to GLUT-1 targeting ligands. The DO2S compound may be optionally labeled with fluorescent, near-infrared imaging probe.

Some embodiments of the invention provide methods for intra-operative diagnosis and treatment of medical conditions by administering to subjects compositions comprising DO2S compounds conjugated to GLUT-1 targeting ligands. The DO2S compound may be optionally labeled with near-infrared imaging probe.

Some embodiments of the invention provide methods for diagnostic imaging of medical conditions. A method comprises administering to a subject a composition comprising a DO2S compound conjugated to a carbohydrate targeting ligand. The DO2S compound may be chelated to a radiometal species.

Some embodiments of the present invention relate to kits for the treatments or diagnosis of a subject. A kit of the invention may comprise a composition comprising a DO2S compound conjugated to a carbohydrate. The DO2S compound may be optionally chelated to a metal species.

BRIEF DESCRIPTION OF DRAWINGS

FIG. 1 illustrates the structure of compound 1a

FIG. 4 illustrates results of cellular uptake study of $^{68}$Ga-labeled compound 1a.

FIG. 5 illustrates results of cellular uptake study of $^{177}$Lu-labeled compound 1a.

FIG. 10 illustrates the structure of compound 2a

FIG. 12 illustrates the radio-TLC of compound 2a

FIG. 13 illustrates the cellular accumulation of $^{68}$Ga-2a.

FIG. 14 illustrates the cellular accumulation and blocking of $^{68}$Ga-2a

FIG. 16 illustrates the results of cellular uptake and blocking study of $^{177}$Lu-2a.

FIG. 41. illustrates structure of compound 7a

FIG. 42. illustrates the ESI-MS spectra of the compound 7a.

DETAILED DESCRIPTION

Figure 1:
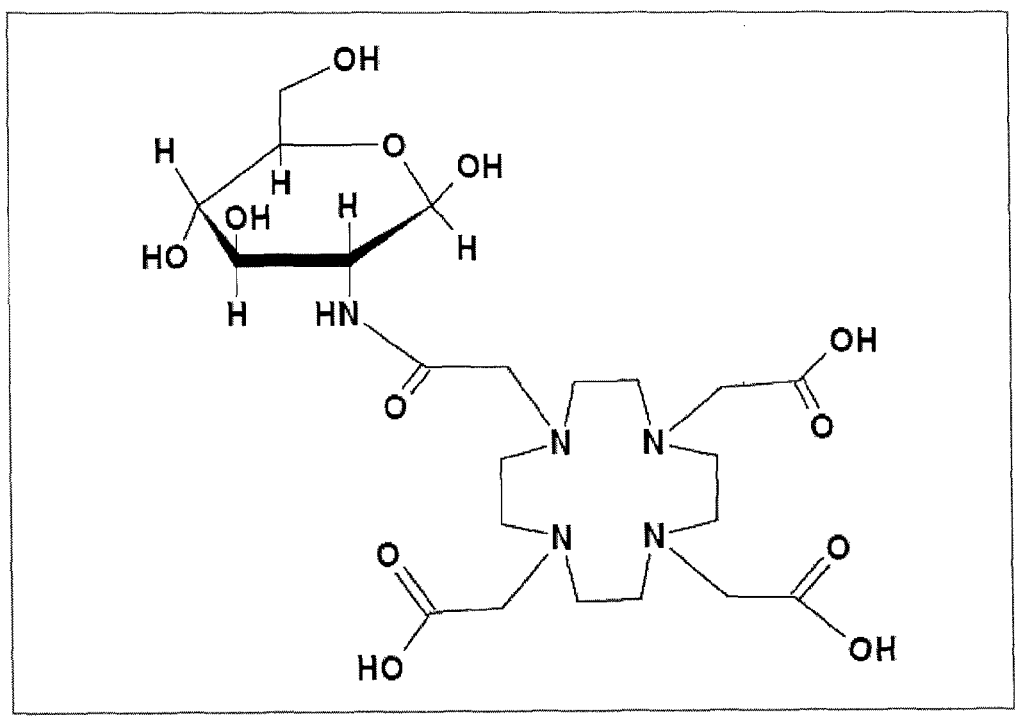
Figure 2:
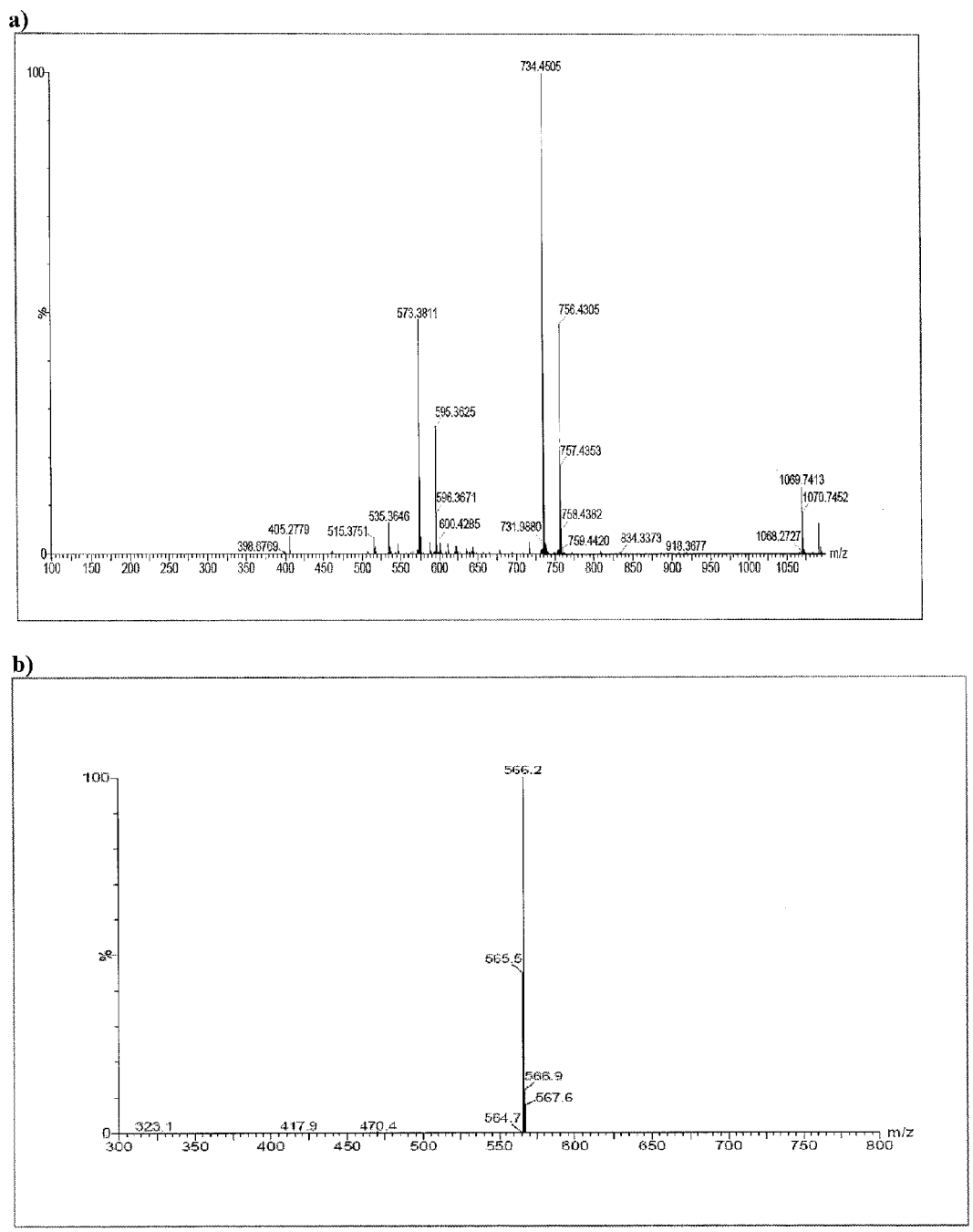
FIG. 2 illustrates the ESI spectra of the t-Bu ester protected compound 1a before the final deprotection (a) and after final deprotection (b). Compound was analyzed using electrospray ionization mass spectroscopy (ES) in the presence of MeOH: 0.2% of formic acid. The ESI spectra showed mass peak corresponding to compound m/z=566.2 (calculated MW+H=565.37). The m/z=734.45 corresponds to compound 1a before the deprotection.
Figure 3:
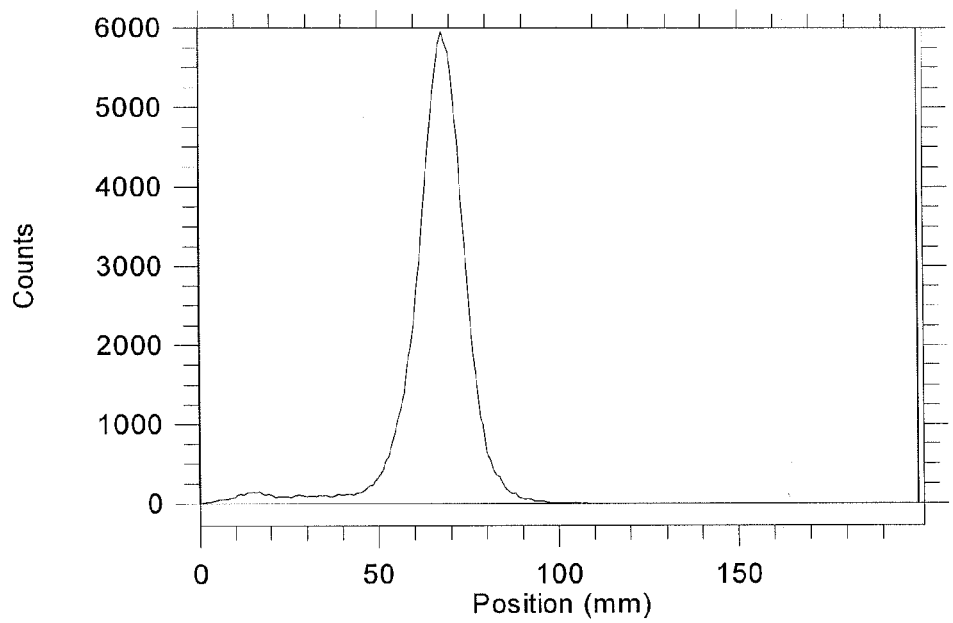
FIG. 3 illustrates radio-TLC of compound 1a. Retention factor for radiolabeled Glucomedix and $^{68}$GaCl$_3$ were 0.9 and 0.1, respectively. Radio-TLC (Bioscan) analysis showed the radiochemical purity of tracer was >97%.
Figure 4:
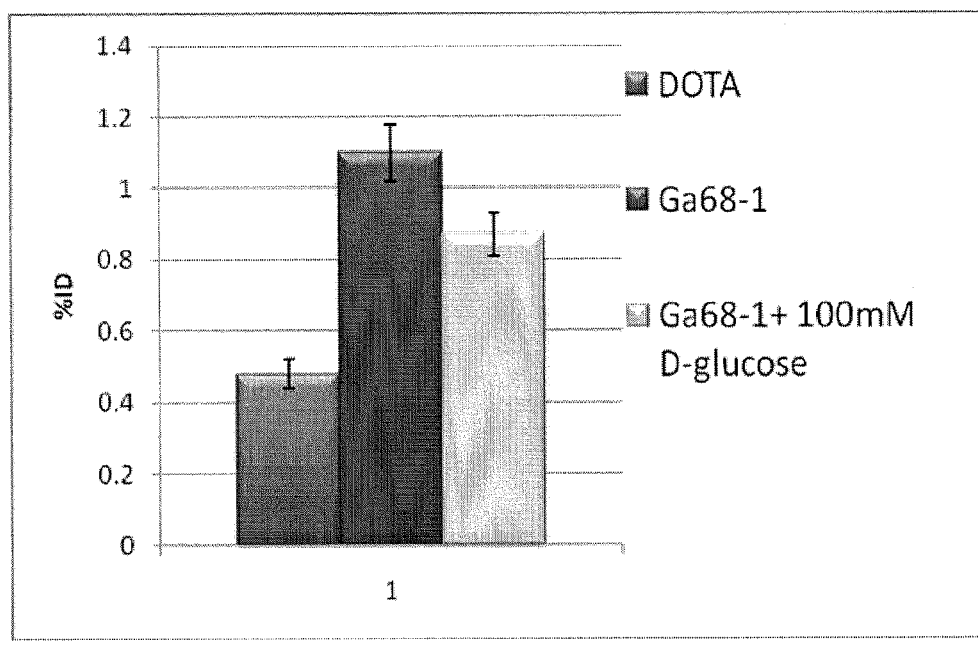
Figure 5:
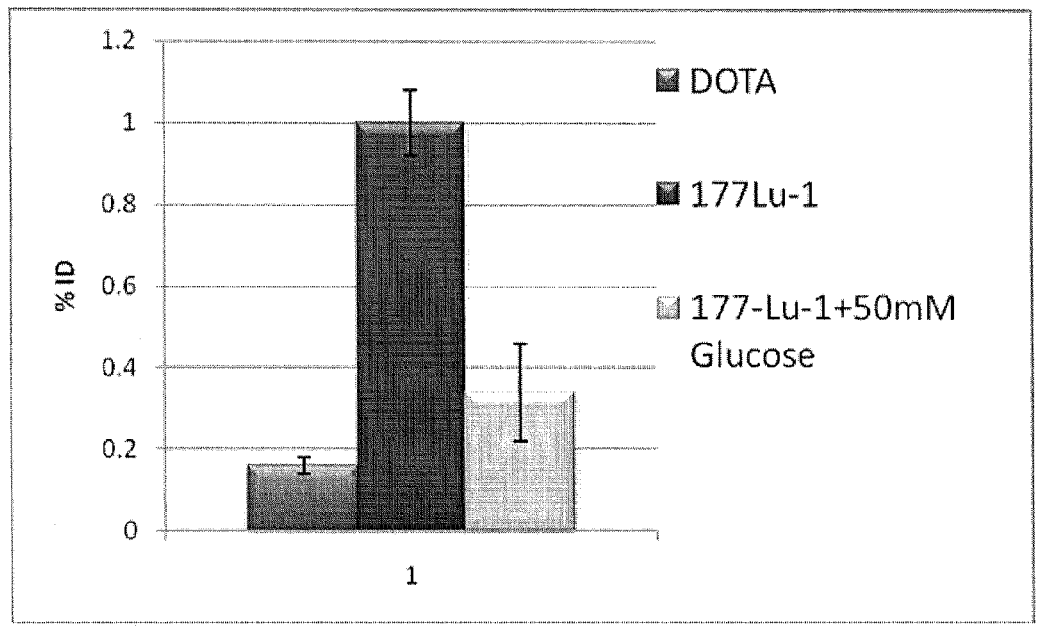
Figure 6:
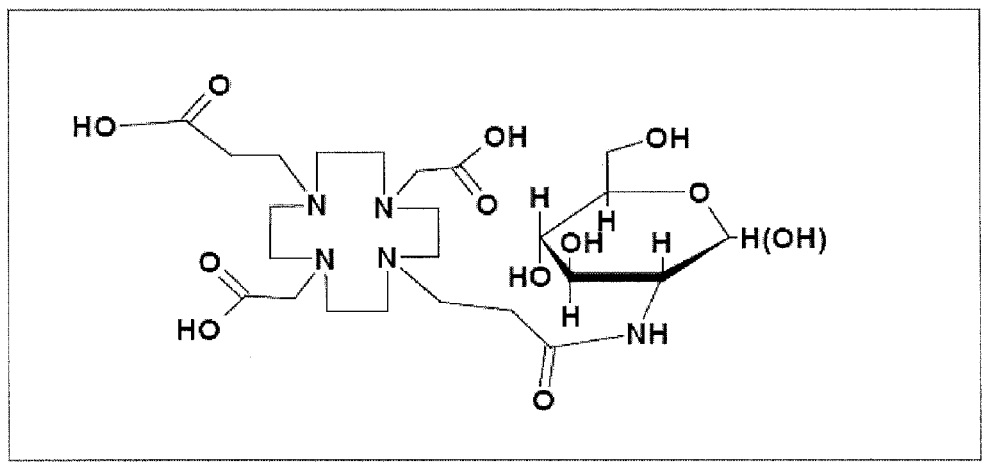
FIG. 6 illustrates the structure of compound 1b.
Figure 7:
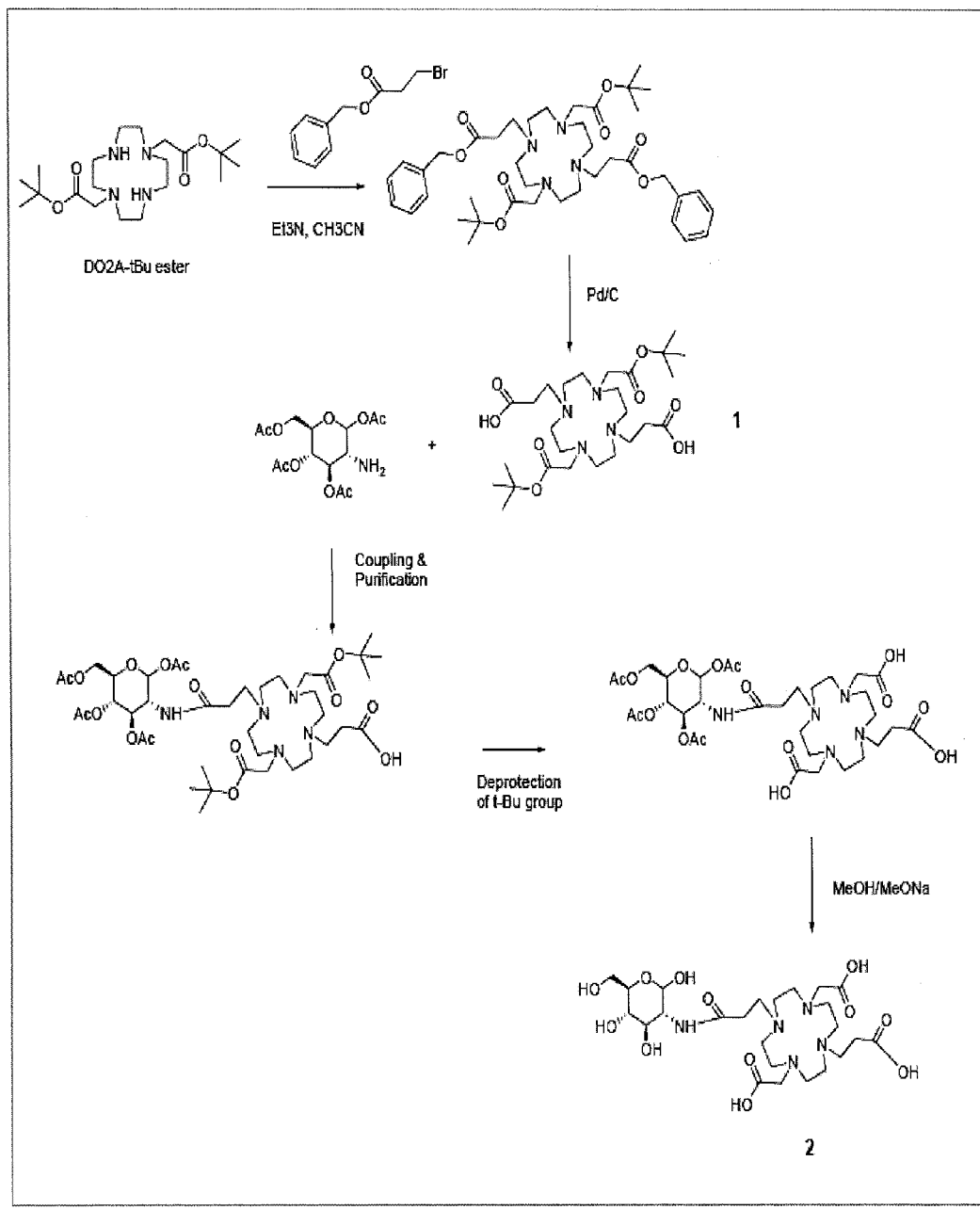
FIG. 7 illustrates a method of synthesis for compound 1b.

Embodiments of the invention relate to chelator-based carbohydrate derivatives and method of their synthesis. Chelator-carbohydrate (DO2S-carbohydrate) maybe synthesized from the amino-sugar is directly conjugated to DO2S compound, or it can be coupled to DO2S through any type of the linker (DO2S-linker-carbohydrate).

In accordance with some embodiments of the invention, synthesis of DO2S-carbohydrate can be performed manually on solid phase and using automated instrument, such as a peptide synthesizer.

Resins used for the solid phase synthesis maybe selected from the group consisting of chloro- and bromofunctionalized (Merrifield, 4-bromomethylphenoxy)methyl polystyrene, 2-(4-bromomethylphenoxy)ethyl polystyrene, trityl, 2-chlortrityl chloride, NovaSyn TGT alcohol, NovaSyn TGT bromo), amino- and hydrazine functionalized (AM polystyrene and N-methyl aminomethylpolystyrene, NovaSyn TG amino, MBHA polystyrene, Rink Amide, Siber, amino trityl, sulfamyl-based, WeinrebAM, Fmoc-4-hydrazinobenzoyl, NOVAGel, alkylaminomethyl-indole, hydroxylamine Wang), hydroxyl functionalized (NovSyn hydroxyl, hydroxymethyl-phenyl, oxime), carboxy, aldehyde (benzyloxybenzaldehyde, FMPB AM, FMPB Nova-Gel, NOVAPEG FMBP, FMPE, DFPE, 3-formylindoyl) acetamidomethyl polystyrene—FIA AM resin), enol functionalized (DHP HM resins), thiol functionalized (mercaptomethyl, 3-[4-tritylmercapto)phenylpropionyl AM resins), carbonate functionalized, alkenylcarbonyl functionalized.

Linkers used for the solid phase synthesis of maybe selected from the group of amino acids, peptides, amino alcohols, polyethylylene glycols, alkanes, alkenes, alkynes, azide aromatic compounds, carbohydrates, carboxylic acids, esters, fosfororganic compounds, sulfonates.

A targeting ligand may be selected from the group consisting of a carbohydrate, peptide, protein, antibody, nucleoside, nucleotide, heterocyclic compound, or alcohol.

Preferred targeting ligands include carbohydrates, such as 2-deoxyglucose, 1'amino-sugar, 2'amino-sugar, 1'2'-amino-sugar, 2'-amino-methylglycoside etc.

The radiometal may be a transition metal ion or lanthanide series element. For example, it may be $^{45}$Ti, $^{59}$Fe, $^{60}$Cu, $^{61}$Cu, $^{62}$Cu, $^{64}$Cu, $^{67}$Cu, $^{67}$Ga, $^{68}$Ga, $^{89}$Sr, $^{90}$Y, $^{99m}$Tc, $^{111}$In, $^{153}$Gd, $^{153}$Sm, $^{166}$Ho, $^{186}$Re, $^{177}$Lu, $^{188}$Re, $^{211}$At, $^{212}$Bi, $^{225}$Ac.

Generally, it is believed that virtually any α-emitter, β-emitter, γ-emitter, or β/γ-emitter can be used in conjunction with embodiments of the invention. Preferred α-emitters include $^{211}$At, $^{212}$Bi and $^{223}$Ra. Preferred β-emitters include $^{90}$Y and $^{225}$Ac. Preferred β/γ-emitters include $^{67}$Cu, $^{89}$Sr, $^{153}$Sm, $^{166}$Ho, $^{177}$Lu, $^{186}$Re and $^{188}$Re. Preferred γ-emitters include $^{62}$Cu, $^{64}$Cu, $^{67}$Ga, $^{68}$Ga, $^{94m}$Tc, $^{99m}$Tc and $^{111}$In. It is also envisioned that paramagnetic substances, such as Gd, Mn, Cu or Fe can be chelated with DO2S derivatives for use in conjunction with embodiments of the present invention.

Embodiments of the present invention provide compositions for tissue specific disease imaging and radiotherapy. The disease may be cardiovascular disease, infection, diabetes, or cancer. In a preferred embodiment, the disease is cancer. The cancer may be a solid tumor. In other specific embodiments, the tumor derives, either primarily or as a metastatic form, from cancers such as of the liver, prostate, pancreas, head and neck, breast, brain, colon, adenoid, oral, skin, lung, testes, ovaries, cervix, endometrium, bladder, stomach, and epithelium.

Embodiments of the invention also provide kits for preparing a radiopharmaceutical preparation. The kit generally includes a sealed vial or bag, or any other kind of appropriate container, containing a predetermined quantity of DO2S-carbohydrate conjugate. The components of the kit may be in any appropriate form, such as in liquid, frozen or dry form. In preferred embodiments, the kit components may be provided in lyophilized form. The kit may also include an antioxidant and/or a scavenger. The antioxidant may be any known antioxidant but is preferably vitamin C. Scavengers may be DTPA, EDTA or DOTA.

EXAMPLES

The following examples are provided to illustrate various aspects of the invention, and are not to be construed as limiting the scope of the invention in any manner.

Example 1

A. Synthesis of 1-N-[1,4,7,10-Tetraazacyclododecane-4,7,10-tetra(acetyl)]-2-amino-2-deoxyglucopyranoside (Compound 1a)

A.1. Direct Coupling of glucosamine hydrochloride to 1,4,7,10-tetraazacyclododecane-1,4,7,10-tetraacetic acid mono-N-hydroxysuccinimide ester (DOTA-NHS)

Sodium methanolate (3eq.) in methanol was added to glucosamine hydrochloride (1eq. Sigma Aldrich) and stirred for 30 min at room temperature. Solvent was evaporated and free glucosamine was added to a solution of DOTA-NHS (1 eq., Macrocyclics) in $ddH_2O$ in phosphate buffer pH=7. Reaction was stirred at room temperature for 48 h, followed by evaporation of solvent under high vacuum. Product was purified by dialysis using Sep-Pak dialysis filters with MW cut off 500 and precipitated by addition of diethyl ether.

A2. Coupling of 1,3,4,6-tetra-O-acetyl-β-D-glucosamine hydrochloride to DOTA tris-t-butyl ester Step a. Preactivation of DOTA Chelating Agent To activate the carboxyl groups, 1,4,7,10-tetraazacyclododecane-1,4,7-tris(t-butyl acetate)-10-acetic acid (1eq.) was dissolved in 2 mL dimethylformamide (DMF), and then N-hydroxybenzotriazole (HOBT) and O-Benzotriazole-N,N,N',N'-tetramethyl-uronium-hexafluoro-phosphate (HBTU) coupling agents (4eq. each) were added in the presence of 4eq. of N,N-diisopropylamine (DIPEA). Reaction was left at room temperature for 30 min.

Step b. Coupling of Glucosamine Hydrochloride to Activated Chelating Agent

Glucosaminehydrochloride (4eq) was dissolved in DMF in the presence of DIPEA (4eq) and added to the solution of pre-activated DOTA. Reaction was left stirring for 48 h at room temperature and was monitored by TLC (chloroform:methanol 1:10) and visualized using anisidine solution or dichlorofluoresceine. Conjugate was purified by extraction using $CH_2Cl_2{:}H_2O$ and organic fraction was collected. The tert-butyl ester protecting groups were removed in the presence of 30% $TFA{:}CH_2Cl_2{:}H_2O{:}TIS$ (950:250:250), and the product was dialyzed using Sep Pak in millipore water for 48 h at room temperature.

A.3. $^{68}$Ga-Radiolabeling of Compound 1a

Compound 1a (1-100 ug) dissolved in 100 ul of ultra pure $ddH_2O$ and 500 ul of 0.5M NaOAc buffer (pH=4.4). 0.5-10 mCi of $^{68}GaCl_3$ was added (eluted from the ITG $^{68}Ge/^{68}Ga$ generator using 0.05M HCl). The final pH of the reaction was 4.1-4.4. The reaction mixture was heated at 70-75° C. for 20 min. After cooling to room temperature, the reaction was analyzed by radio-TLC.

A.4. In Vitro Evaluation of $^{68}$Ga-Compound 1a a) Cellular uptake study of $^{68}$Ga-compound 1a. A549 cells were plated in 12 well plates at a density of $1.5 \times 10^5$ cells per well and grown overnight in DMEM containing 5.4 mg/ml glucose and 10% FBS at 37° C., 5% $CO_2$. Cells were fasted for 30 min prior to the study with glucose free DMEM. At the start of the study, media was removed from each well and replaced with 0.5 ml glucose free DMEM (Cellgro) containing 0.5 microCi $^{68}$Ga-1a or $^{68}$Ga DOTA or DMEM media containing 10 mmD-glucose (or other GLUT1 inhibitors such as genistein, scutellarin, cytochalasin B) and 0.5 microCi$^{68}$GA-1a. Cells were incubated at 37° C., 5% $CO_2$ for the indicated time. The radioactive media were then removed and cells were washed twice with 1 ml PBS. Cells were then trypsinized and radioactivities were counted. Data is expressed as % ID (cpm cells/cpm media*100). Error bars represent Standard deviation.

b). Cellular uptake study of $^{177}$Lu-compound 1a. LS174T cells were plated in 12 well plates at a density of $1.5 \times 10^5$ cells per well and grown overnight in DMEM containing 5.4 mg/ml glucose and 10% FBS at 37° C., 5% $CO_2$. Cells were fasted for 30 min prior to the study with glucose free DMEM. At the start of the study, media were removed from each well and replaced with 0.5 ml glucose free DMEM (Cellgro) containing 0.5 microCi $^{177}$Lu-1a or $^{177}$Lu-DOTA or DMEM media containing 10 mmD-glucose and 0.5 microCi $^{177}$Lu-1a. Cells were incubated at 37° C., 5% $CO_2$ for the indicated time. The radioactive media were then removed and cells were washed twice with 1 ml PBS. Cells were then trypsinized and radioactivities were counted. Data is expressed as % ID (cpm cells/cpm media*100). Error bars represent Standard deviation.

Example 2

B.1. Synthesis of N-[1,4,7,10-Tetraazacyclododecane-1,7-bis-(propionic acid)-4,10-bis(acetic acid)]-2-amino-2-deoxyglucopyranoside (Compound 1b)

Step. 1. Modification of 1,4,7,10-tetraazacyclododecane-1,7-bis(t-butyl acetate)

1,4,7,10-tetraazacyclododecane-1,7-bis(t-butyl acetate), DO2A tBu ester (1eq., Macrcyclics) was dissolved in $CH_3CN$ (5 ml) and benzyl 3-bromopropanoate was added in the presence of Et3N (2.1 ml, 12 mmol) at temp. 0° C. Reaction was slowly warmed up to room temp. and left stirring for 24 h. After evaporation of the solvent under vacuum, product was purified by flash chromatography using 60N silica gel. Deprotection of benzyl ester groups was completed by catalytic hydrogenation under high pressure in the presence of Pd/C during 24 h.

Step 2. Preactivation and Functionalization of 1,4,7,10-tetraazacyclododecane-1,7-bis(t-butyl acetate)-4,10-bis(propionic acid)

Modified chelating agent was dissolved in DMF (3 mL) in the presence DIPEA (3eq) and coupling agent, HBTU (3eq.) was added to the solution. The mixture was left for 20 min at r.t. GlcNAc-b-$NH_2$ (1.3 eq.) was dissolved in DMSO (1 ml). The solution was heated slightly to dissolve the monosaccharide and added to the pre-actived DO2A chelating agent. The mixture was allowed to react at room temp. with constant stirring 12 h. After solvent evaporation, product was purified by extraction using $CHCl_3$:MeOH and flash silica gel 60N column.

Step 3. Removal of tBu Ester Protecting Groups

The tert-butyl ester protecting groups were removed in the presence of 30% TFA:$CH_2Cl_2$:$H_2O$:TIS (950:250:250).

B.2. $^{68}$Ga-Labeling of Compound 1b

Radiolabeling was performed in 0.5M NaOAc pH=4.4 at 80° C. for 20 min. iTLC was developed in standard running buffer (0.5M NH4OAC:methanol 1:1 v/v). Radio-TLC (Bioscan) analysis showed the radiochemical purity of tracer was >98%.

Example 3

C.1. Synthesis of N,N-[1,4,7,10-tetraazacyclododecane-1,4,7,10-tetra-(acetyl)]-1,7-di-(2-amino-2-deoxy-β-D-glucopyranoside (Compound 2a)

This is a two step synthesis performed by coupling of glucosamine hydrochloride to 4,7,10-tetraazacyclodo decane-1,4,7,10-tetraacetic acid.

Step a. Preactivation of DOTA Chelating Agent

To activate the carboxyl groups, 1,4,7,10-tetraazacyclododecane-1,4,7,10-tetraacid acetic acid (1eq.) was dissolved in 2 mL N-methylpyrolidine (NMP) and HATU coupling agent (4eq.) was added in the presence of 4eq. of N,N-diisopropylamine (DIPEA). Reaction was left at room temperature for 20 min.

Step b. Coupling of Glucosamine Hydrochloride to Activated Chelating Agent

Glucosamine hydrochloride (4eq) was dissolved in NMP in the presence of DIPEA (4eq) and added to the solution of pre-activated DOTA. Reaction was left stirring for one day at room temperature and was traced by TLC (chloroform: methanol 1:10) visualized using anisidine solution or dichlorofluoresceine. After concentration of the reaction under high vacuum, product was extracted using CH2Cl2:H2O and aqueous fraction was collected. Final product was precipitated by addition of ether diethyl on ice.

C.2. $^{68}$Ga-Labeling of Compound 2a

Figure 8:
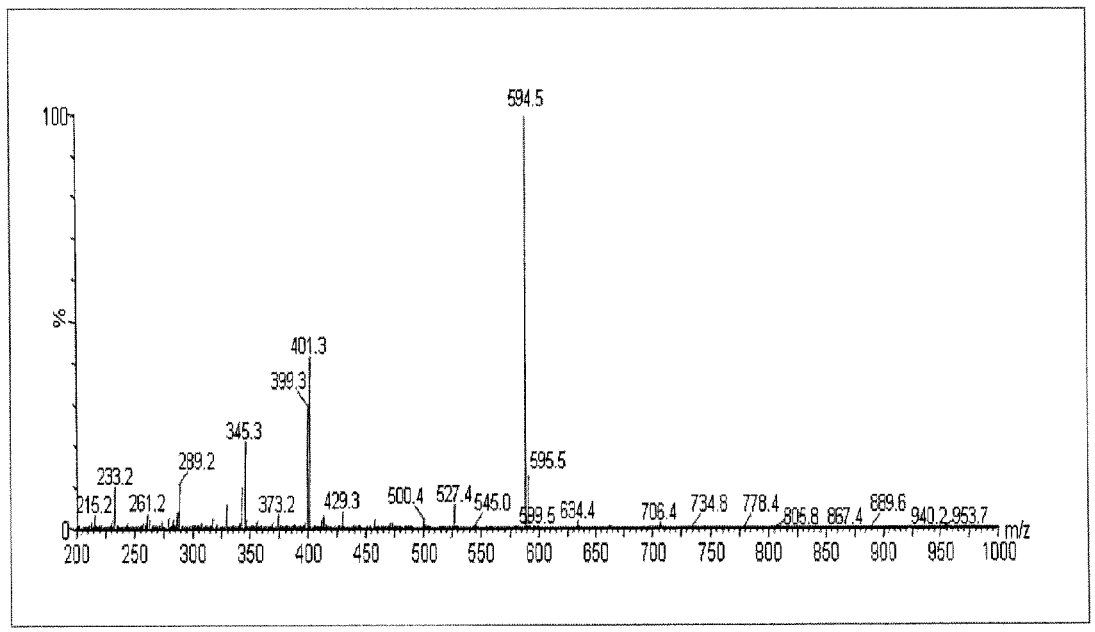
FIG. 8 illustrates the ESI-MS spectra of compound 1b. m/z=593.62 for [M+H] and calculated for $C_{24}H_{43}N_5O_{12}$ [M+1]=595.5
Figure 9:
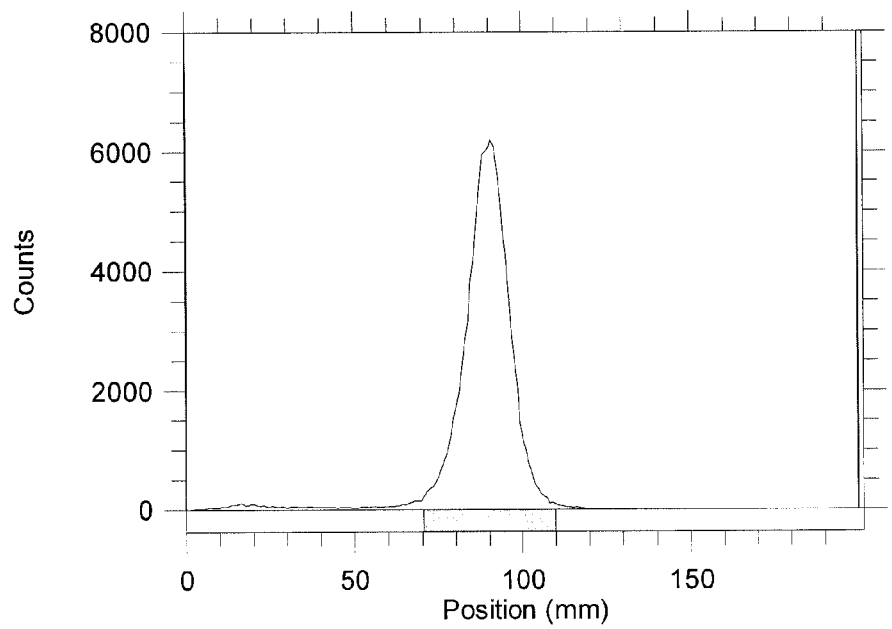
FIG. 9 illustrates the radio-TLC of compound 1b.
Figure 10:
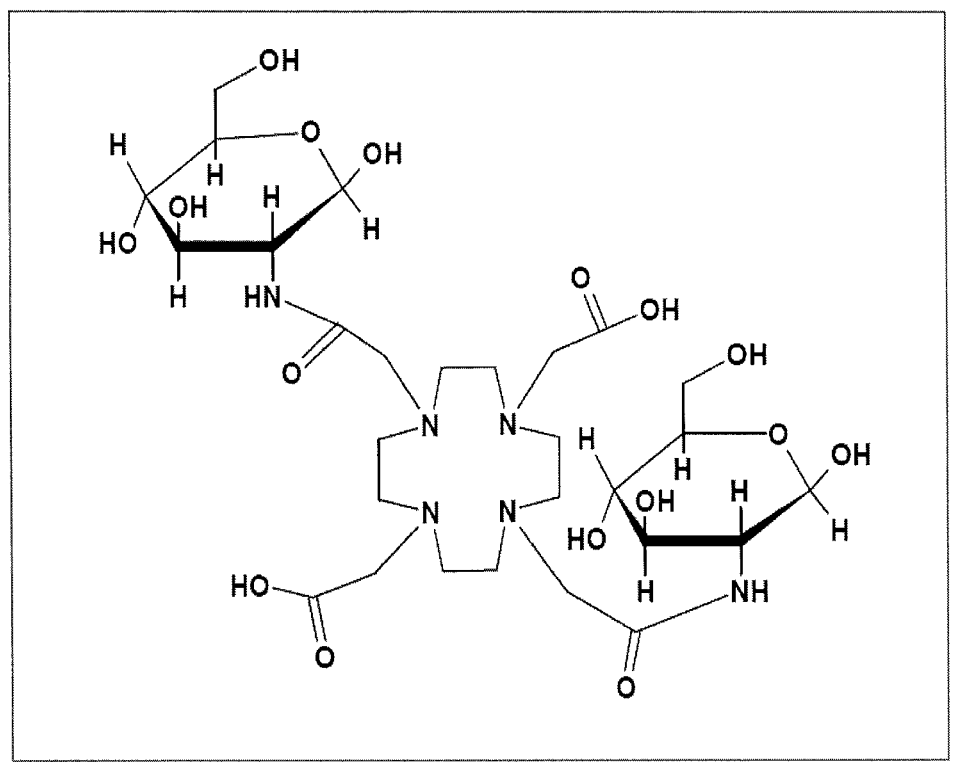
Figure 11:
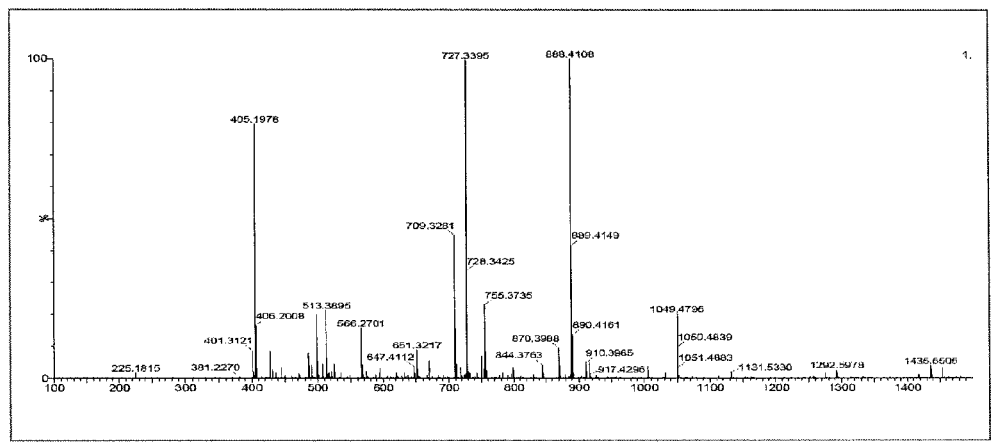
FIG. 11 illustrates the ESI-MS spectra of compound 2a before (a) and after purification (b) shown below m/z=727.33 for [M+H] and calculated for $C_{28}H_{50}N_6O_{16}$ [M]=726.73.
Figure 11:
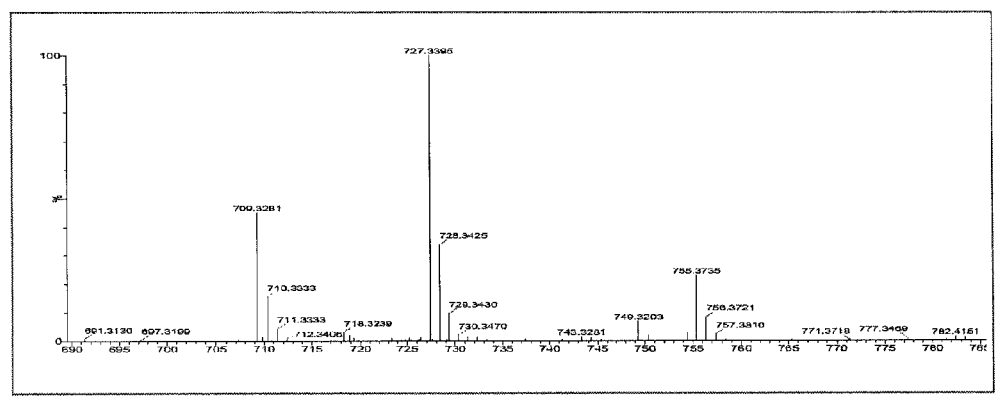
Figure 11:
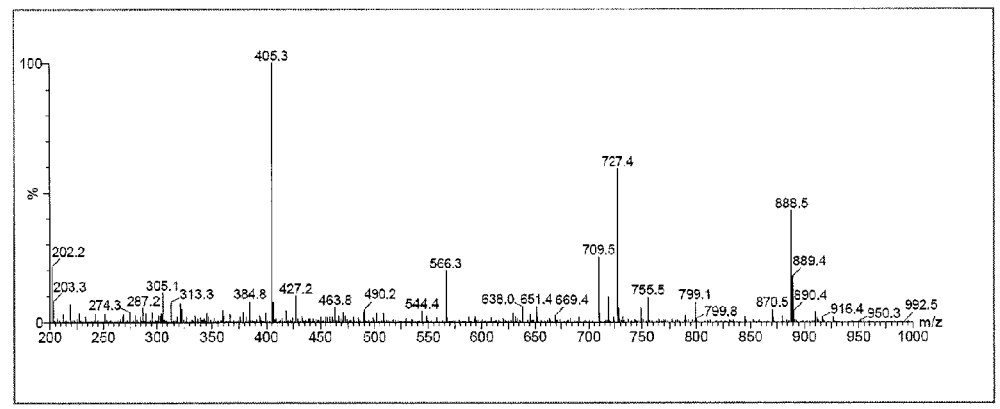
Figure 12:
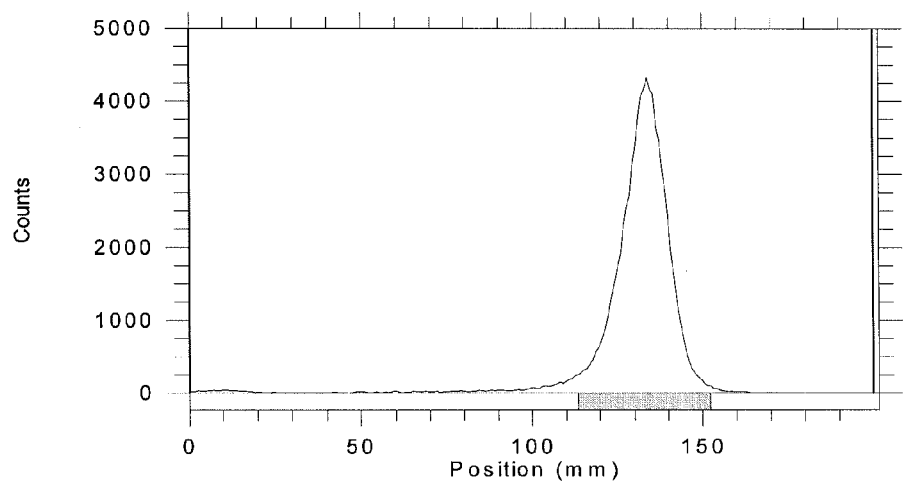
Figure 13:
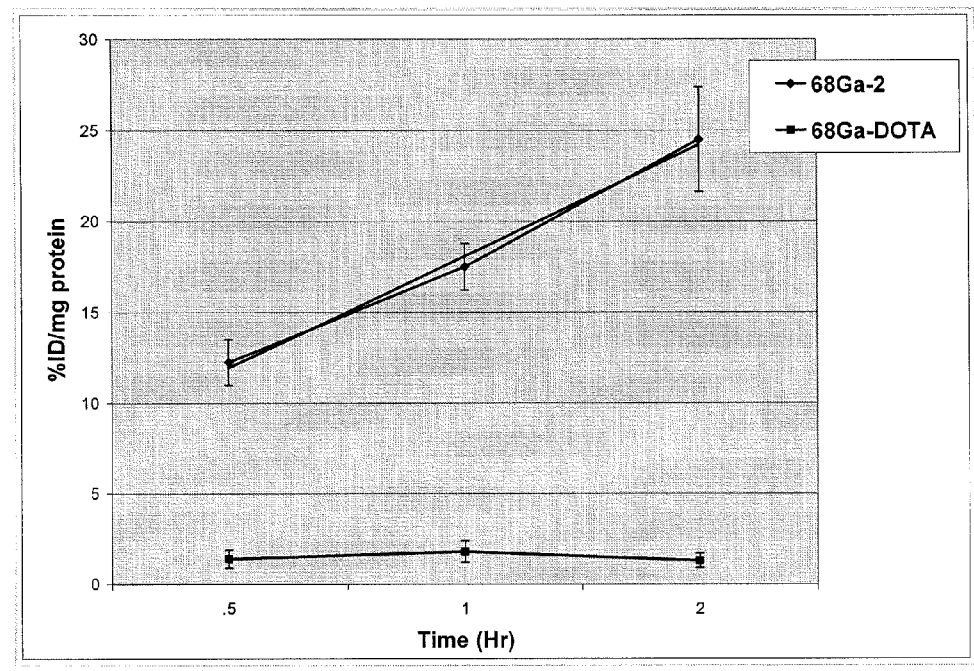
Figure 14:
Figure 15:
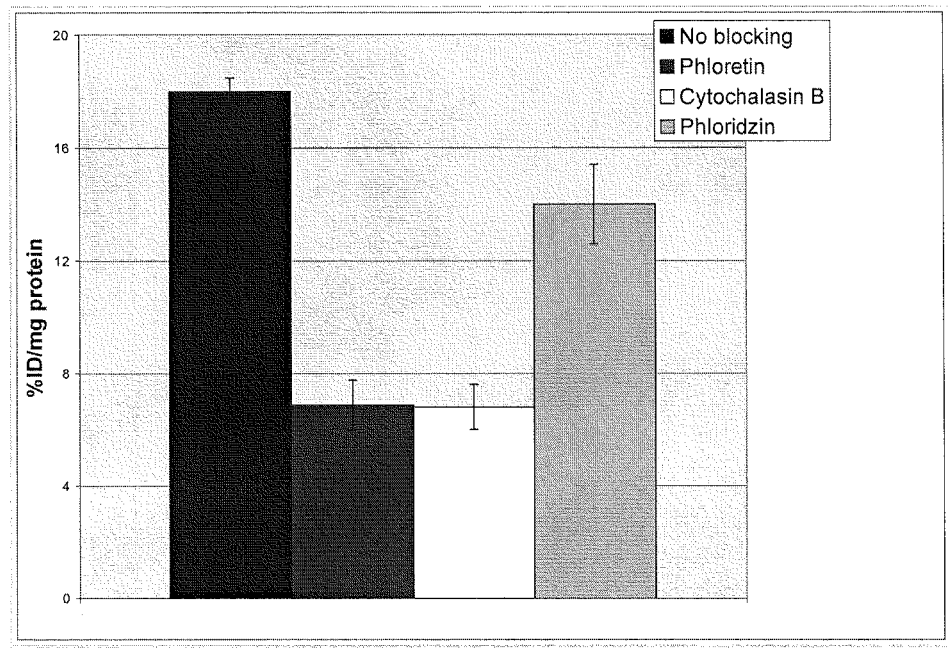
FIG. 15 shows blocking of accumulation of $^{68}$Ga-2a by glucose transporter inhibitors
Figure 16:
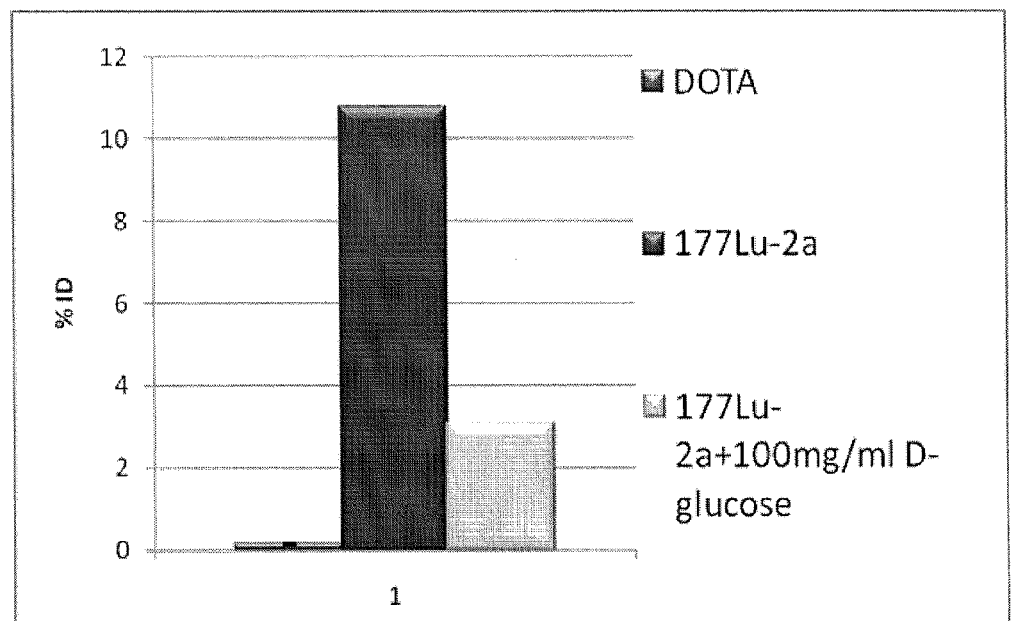
Figure 17:
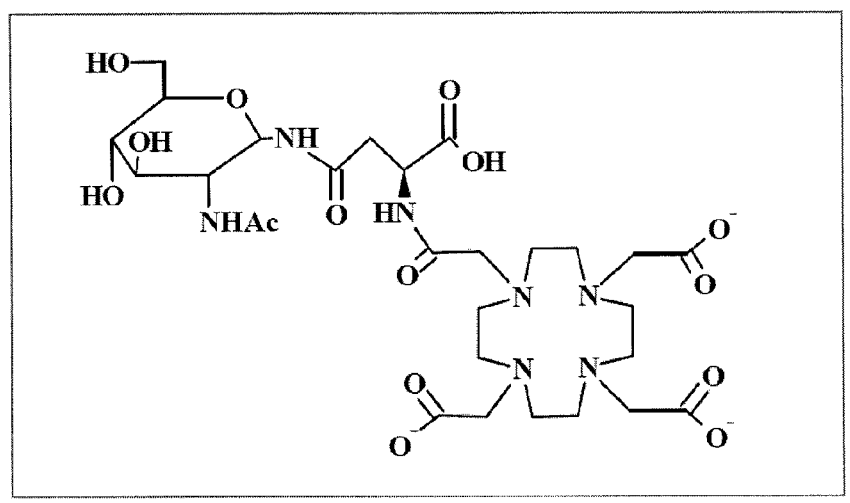
FIG. 17 illustrates the structure of compound 3
Figure 18:
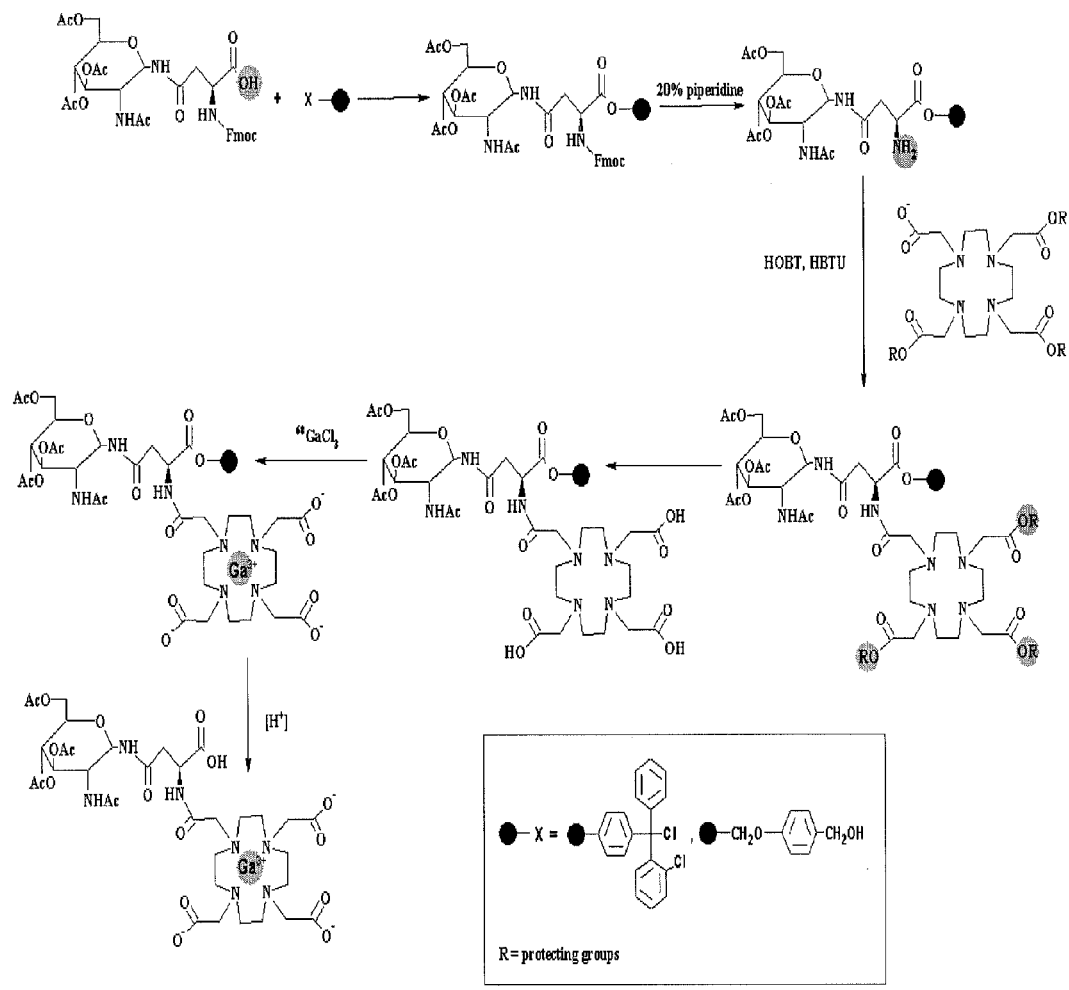
FIG. 18 illustrates methods of synthesis of compound 3
Figure 19:
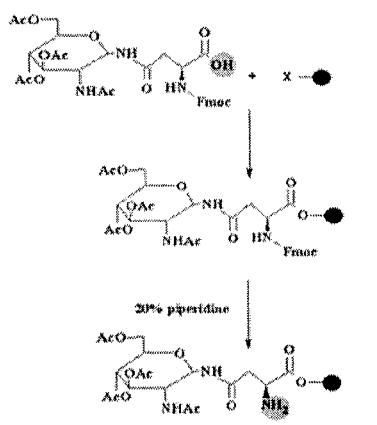
FIG. 19 illustrates loading efficiency
Figure 20:
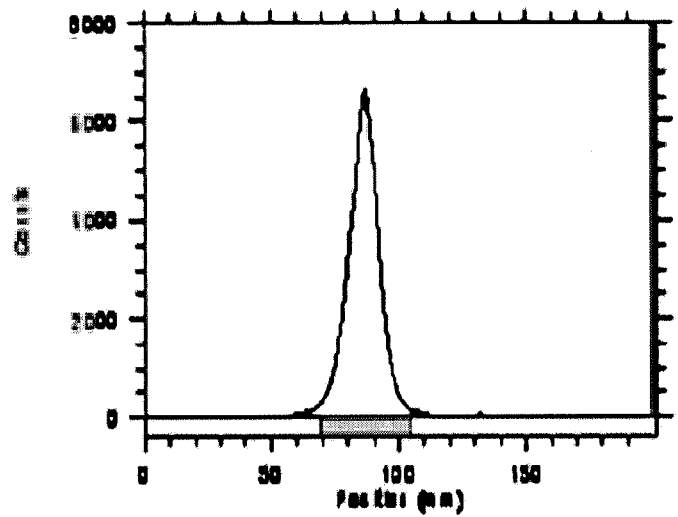
FIG. 20 illustrates the radio-TLC of compound 3
Figure 21:
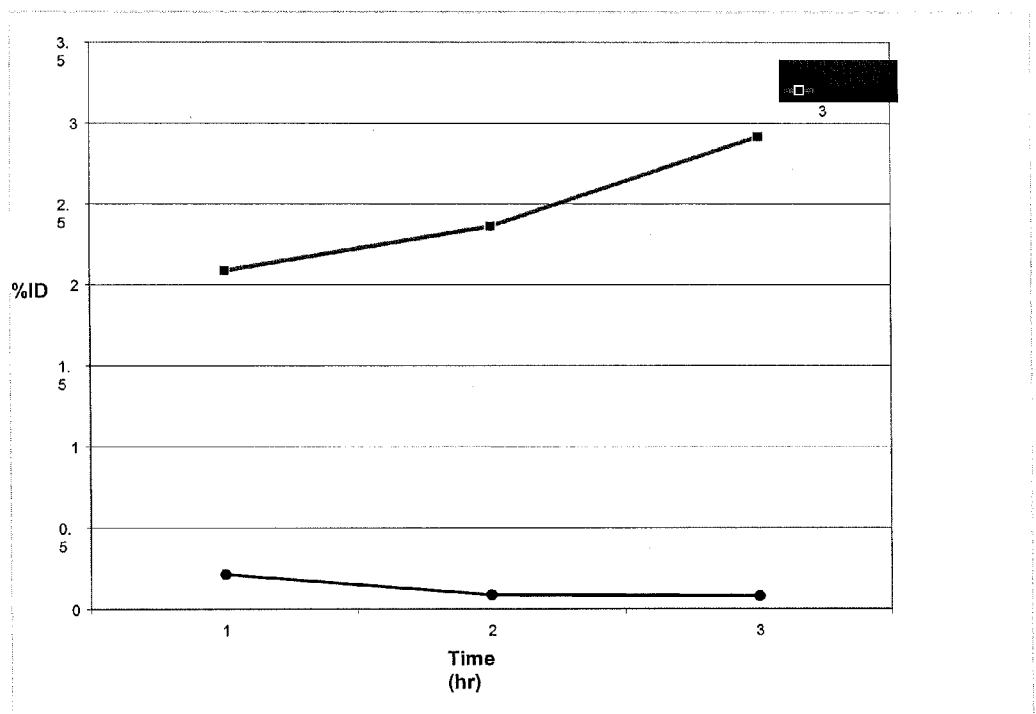
FIG. 21 illustrates the results of cellular accumulation of $^{68}$Ga-3.
Figure 22:
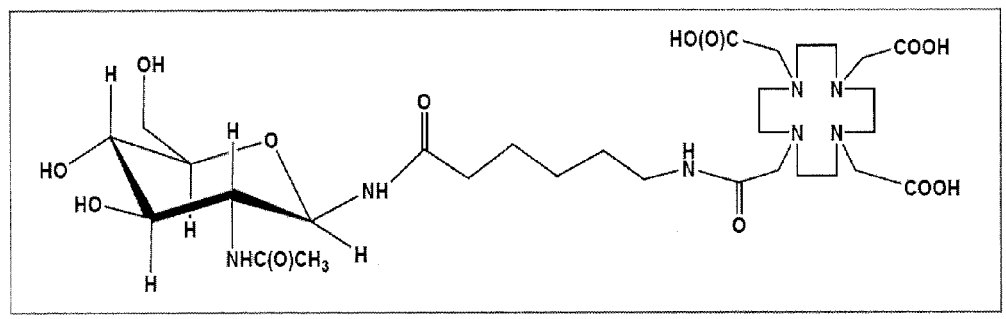
FIG. 22 illustrates the structure of compound 4

Radiolabeling was performed in 0.5M NaOAc pH=4.4 at 65° C. for 20 min. iTLC was developed in standard running buffer (0.5M NH4OAC:methanol 1:1 v/v) and is shown below on FIG. 8. Radio-TLC (Bioscan) analysis showed the radiochemical purity of tracer was >99%

C.3. Cellular Accumulation of $^{68}$Ga-2a

SKBr3 cells were plated in 12 well plates at a density of 2*10^5 cells per well and grown overnight in DMEM containing 5.4 mg/ml glucose and 10% FBS at 37° C., 5% CO2. Cells were fasted for 20 min prior to the study with glucose free DMEM. At the start of the study, media was removed from each well and replaced with 0.5 ml glucose free DMEM (Cellgro) containing 0.5-1 µCi 68Ga-2 or 68Ga DOTA. Cells were incubated at 37° C., 5% CO2 for the indicated time. The radioactive media was then removed and cells were washed twice with 1 ml PBS. Cells were then trypsinized and transferred to counting tubes. Radioactivity in cells and media were counted at 511 keV using a Perkin Elmer Wizard gamma counter. Cells were then collected and lysed with RIPA buffer (Invitrogen) and protein concentration was determined by Pierce BCA protein assay kit (ThermoFisher). Data is expressed as % ID (cpm cells/cpm media*100)/mg protein. Error bars represent Standard deviation.

C.4. Cellular Accumulation and Blocking of $^{68}$Ga-2a

SKBr3 cells were plated in 12 well plates at a density of 2*10^5 cells per well and grown overnight in DMEM containing 5.4 mg/ml glucose and 10% FBS at 37° C., 5% CO2. Cells were fasted for 20 min prior to the study with glucose free DMEM. At the start of the study, media was removed from each well and replaced with 0.5 ml glucose free DMEM (Cellgro) or media that contained 100 mg/ml D or L glucose (Sigma Aldrich) and 0.5-1 µCi 68Ga-2. Cells were incubated at 37° C., 5% CO2 for 1 hour. The radioactive media was then removed and cells were washed twice with 1 ml PBS. Cells were then trypsinized and transferred to counting tubes. Radioactivity in cells and media were counted at 511 keV using a Perkin Elmer Wizard gamma counter. Cells were then collected and lysed with RIPA buffer (Invitrogen) and protein concentration was determined by Pierce BCA protein assay kit (ThermoFisher). Data is expressed as % ID (cpm cells/cpm media*100)/mg protein. Error bars represent Standard deviation. Data represents the average of four separate studies performed in triplicate.

C.5. Blocking of Accumulation of 68Ga-2a by Glucose Transporter Inhibitors

SKBr3 cells were plated in 12 well plates at a density of 2*10^5 cells per well and grown overnight in DMEM containing 5.4 mg/ml glucose and 10% FBS at 37° C., 5% CO2. Cells were fasted for 20 min prior to the study with glucose free DMEM. At the start of the study, media was removed from each well and replaced with 0.5 ml glucose free DMEM (Cellgro) or media that contained 100 mg/ml D or L glucose (Sigma Aldrich) or other GLUT1 inhibitors (genistein, cytochalasin B, scutellarin) and 0.5-1 µCi 68Ga-2. Cells were incubated at 37° C., 5% CO2 for 1 hour. The radioactive media was then removed and cells were washed twice with 1 ml PBS. Cells were then trypsinized and transferred to counting tubes. Radioactivity in cells and media were counted at 511 keV using a Perkin Elmer Wizard gamma counter. Cells were then collected and lysed with RIPA buffer (Invitrogen) and protein concentration was determined by Pierce BCA protein assay kit (Thermo-Fisher). Data is expressed as % ID (cpm cells/cpm media*100)/mg protein. Error bars represent Standard deviation. Data represents the average of four separate studies performed in triplicate.

C.6. Cellular Uptake and Blocking Study of 177Lu-2a

A549 cells were plated in 12 well plates at a density of 1.5*10^5 cells per well and grown overnight in DMEM containing 5.4 mg/ml glucose and 10% FBS at 37° C., 5% CO2. Cells were fasted for 30 min prior to the study with glucose free DMEM. At the start of the study, media was removed from each well and replaced with 0.5 ml glucose free DMEM (Cellgro) containing 0.5 microCi $^{177}$Lu-1a or $^{177}$Lu-DOTA or DMEM media containing 10 mg/ml D-glucose and 0.5 microCi $^{177}$Lu-1a. Cells were incubated at 37° C., 5% CO2 for the indicated time. The radioactive media was then removed and cells were washed twice with 1 ml PBS. Cells were then trypsinized and radioactivity was counted. Data is expressed as % ID (cpm cells/cpm media*100). Error bars represent Standard deviation.

Example 4

D.1. Synthesis of N-[1,4,7,10-Tetraazacyclododecane-1,4,7,10-tetra-(acetic acid)]-2-amino-2-deoxyglucopyranoside

Step 1. Coupling

Fmoc-Asn-Glc (0.015 eq.) was immobilized on the 2-chlorotrityl chloride resin (0.01 eq) in the presence of DIPEA (4 eq) in DMF. Reaction is carried out in presence of excess of DIPEA in order to prevent possible hydrolysis of chloro-resin bond and to neutralize HCl, that form during esterification reaction. Reaction is completed with 1-2 h at r.t.

Step 2. Capping

After attachment of Fmoc-Asn-Glc, the unmodified chloride resin was deactivated by addition of ethanol or TFE.

Step 3. Loading Efficiency (Fmoc Titration)

The Fmoc concentration on the resin was determined by addition of 20% piperidine in DMF to the tested resin. The resultant fulvene-piperidine adduct had UV absorption max at 301 nm. Free Fmoc amino acid of know concentration was used as a standard. Loading efficiency of the compound 3 on the resin was close to 15% after 1 h. Loading increased to 79% when reaction was left for more than 24 h. The lower loading of Fmoc-Asn-Glc conjugate relatively to unprotected Asn is probably caused by steric hindrance and close proximity of carboxyl group and Fmoc group. Loading efficiency was also determined using Kaiser test, that measure the content of free amines after Fmoc deprotection.

Step 4. Deprotection-Removal of Fmoc-Protecting

To Fmoc-Asn-Glc attached to the resin 20% piperidine/DMF was added and lefty for 30 min followed by wash with 1 ml of DMF.

Step 4. $^{68}$Ga-Labeling on the Resin

Radiolabeling was performed on the compound still attached to the resin. 200 uCi of 68Ga was added to the suspension of resin in buffer pH=4.4. reaction was mildly heated at 55° C. for 10-12 min.

Step 5. Cleavage from Resin

Conjugate was released from in acid-mediated in mild conditions by addition of AcOH in DCM:H2O:TIS at r.t. in 20-25 min. This process can additionally accelerated in higher temp. The after addition of AcOH to the resin and incubation at room, flow through is collected and pH of the eluate is adjusted to 4.4 by addition of NaOAc buffer.

D.2. Cellular Accumulation of 68Ga-3

A549 cells were plated in 12 well plates at a density of 2*10^5 cells per well and grown overnight in DMEM containing 5.4 mg/ml glucose and 10% FBS at 37° C., 5% CO2. Cells were fasted for 30 min prior to the study with glucose free DMEM. At the start of the study, media was removed from each well and replaced with 0.5 ml glucose free DMEM (Cellgro) containing 0.5 microCi 68Ga-3 or 68Ga DOTA. Cells were incubated at 37° C., 5% CO2 for the indicated time. The radioactive media was then removed and cells were washed twice with 1 ml PBS. Cells were then trypsinized and radioactivity was counted. Data is presented as % cpm cells/cpm media.

D.3. Cellular Accumulation of 68Ga-3

A549 cells were plated in 12 well plates at a density of 2*10^5 cells per well and grown overnight in DMEM containing 5.4 mg/ml glucose and 10% FBS at 37° C., 5% CO2. Cells were fasted for 30 min prior to the study with glucose free DMEM. At the start of the study, media was removed from each well and replaced with 0.5 ml glucose free DMEM (Cellgro) containing 0.5 microCi 68Ga-3 or 68Ga DOTA. Cells were incubated at 37° C., 5% CO2 for the indicated time. The radioactive media was then removed and cells were washed twice with 1 ml PBS. Cells were then trypsinized and radioactivity was counted. Data is presented as % cpm cells/cpm media.

Example 5

E.1. Synthesis. N-1-(ε-aminocaproyl)-β-N-acetyl-2-deoxyglucopyranosyl N-[1,4,7,10-tetraazacyclodecane-1,4,7,10-tetra-(acetyl acid)]

Step 1. Synthesis of β-N-Acetylglucosaminylamine (FIG. 23, compound 3). 2-Acetamido-2-deoxy-beta-D-glucopyranosyl azide 3,4,6-triacetate was obtained from Aldrich and was converted to amine (2) by using PPh3 and DCM following the general literature procedure (Carbohyd. Research, 2001, 331, 439). Deacetylation: To a solution of an acetyl protected amine (2) in dry MeOH, 1-2 drops of ~1M methanolicNaOMe solution were added, and the reaction mixture was kept at rt until completion of the transformation (monitored by tlc). Amberlyst 15 (H+ form) resin was then added to remove sodium ions, the resin was filtered off, and the solvent removed in vacuo.

Step 2. Synthesis of N-(ε-aminocaproyl)-β-N-acetylglucosaminylamine (FIG. 23, compound 5). 6-Trifluoroacetamido-hexanoic acid (1 eq.) was dissolved in DMSO (0.6 ml). DIEA (6 eq.) and HBTU (1.3 eq.) were added to the solution. The mixture was allowed to pre activate for approximately 10 min. In a separate vial GlcNAc-b-NH2 (1.3 eq) was dissolved in DMSO (1.3 ml). The solution was heated slightly to dissolve the monosaccharide. After the solution was cooled to rt, the monosaccharide solution was added to the activated solution. The mixture was allowed to react to rt with constant stirring for 3 h. Final product was purified by flash using silica gel 60N.

Figure 23:
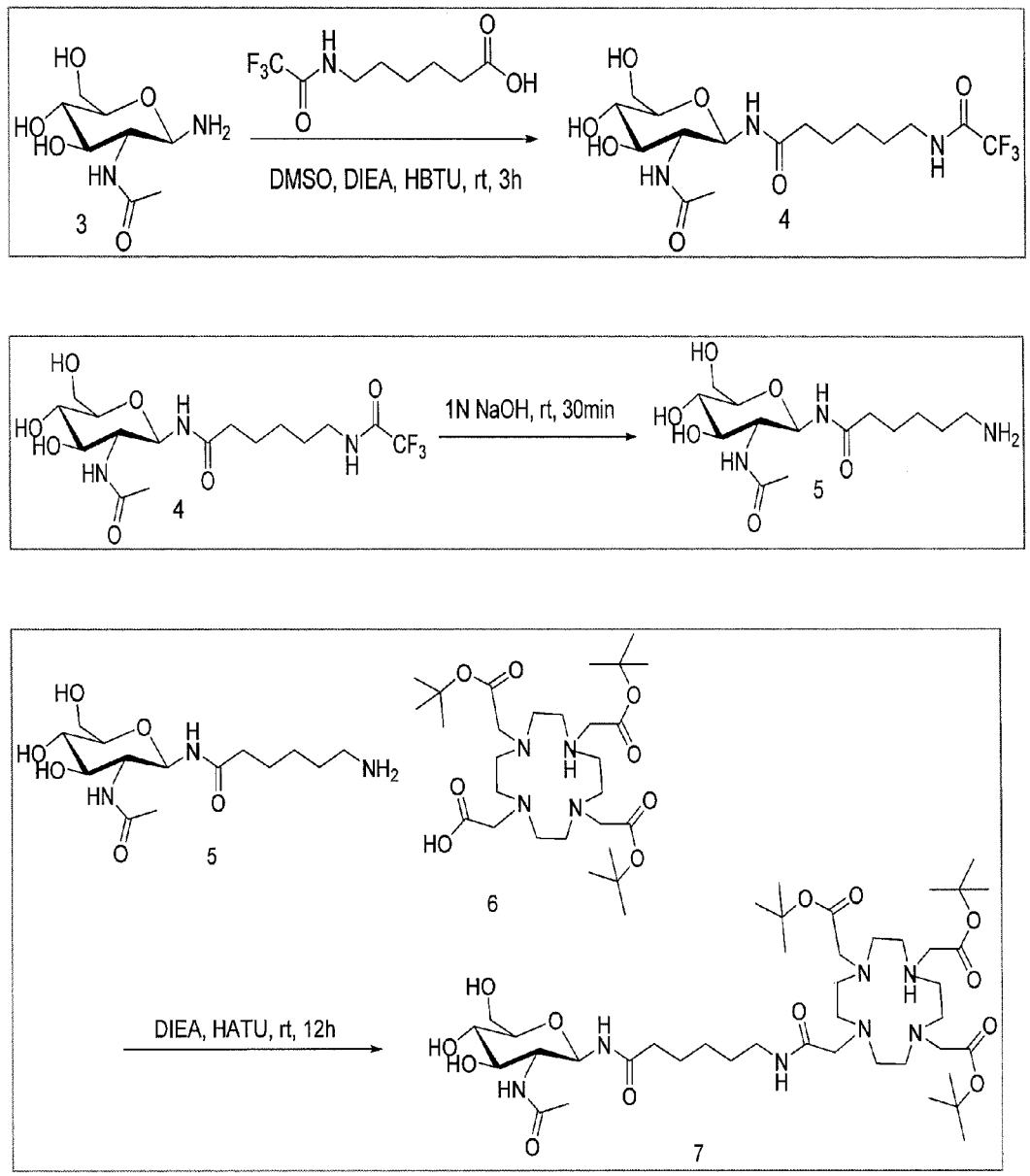
FIG. 23 illustrates of a method of synthesis of compound 4
Figure 24:
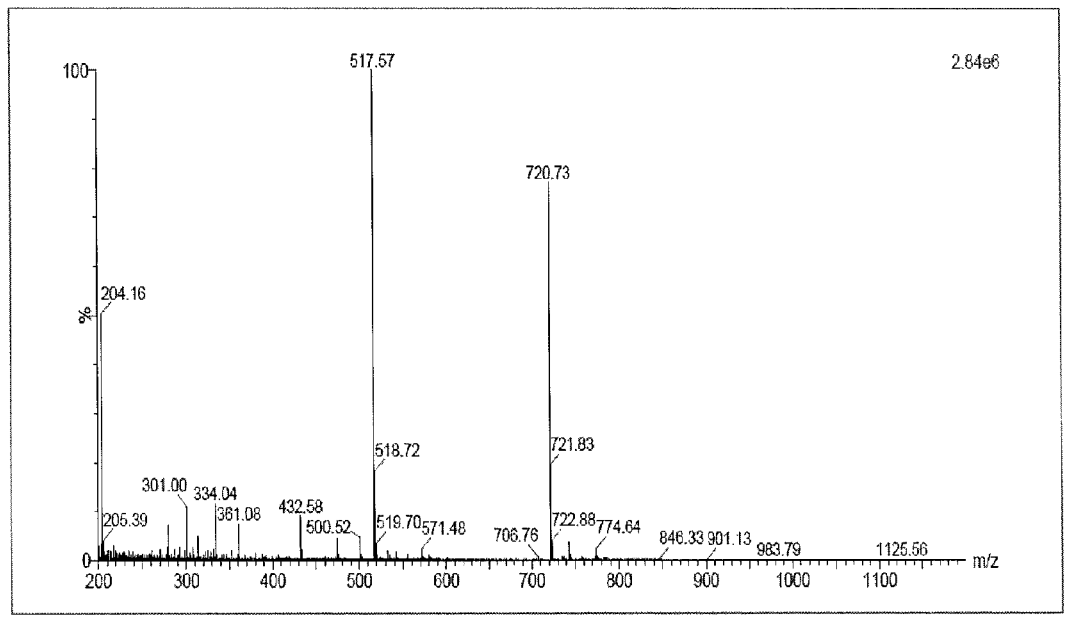
FIG. 24 illustrates the ESI-MS spectra of compound 4, m/z=720.73 for [M+H] and calculated for compound 4 m/z=719.2
Figure 25:
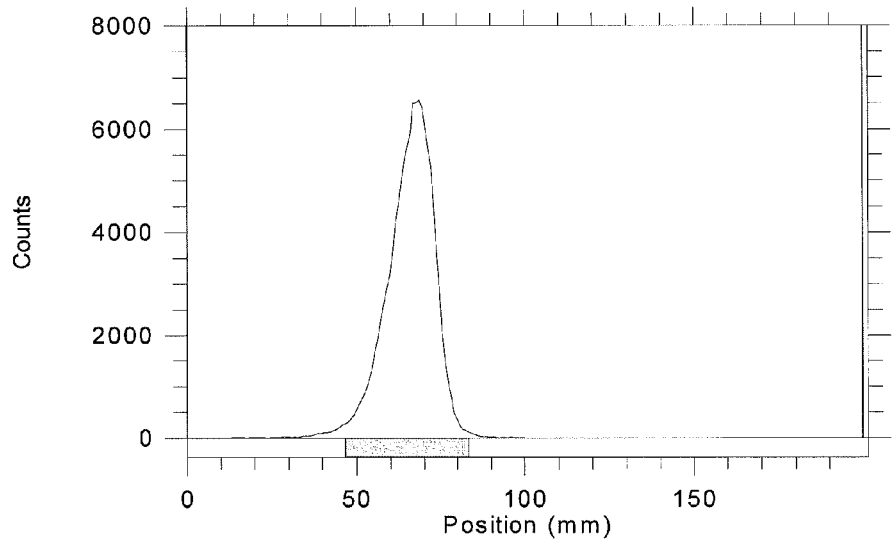
FIG. 25 illustrates the radio-TLC of compound 4
Figure 26:
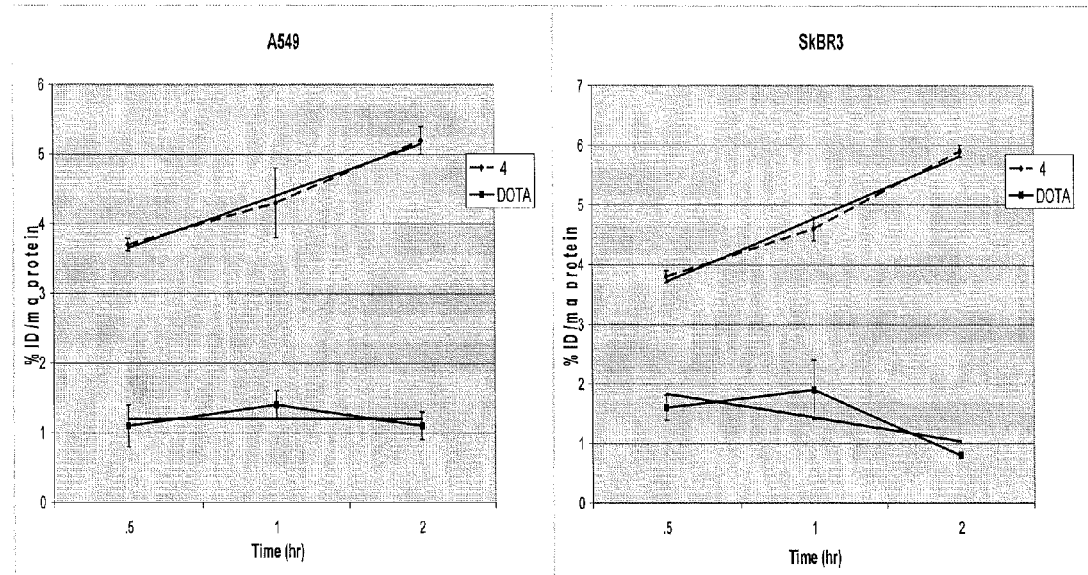
FIG. 26 illustrates cellular accumulation of $^{68}$Ga-4
Figure 27:
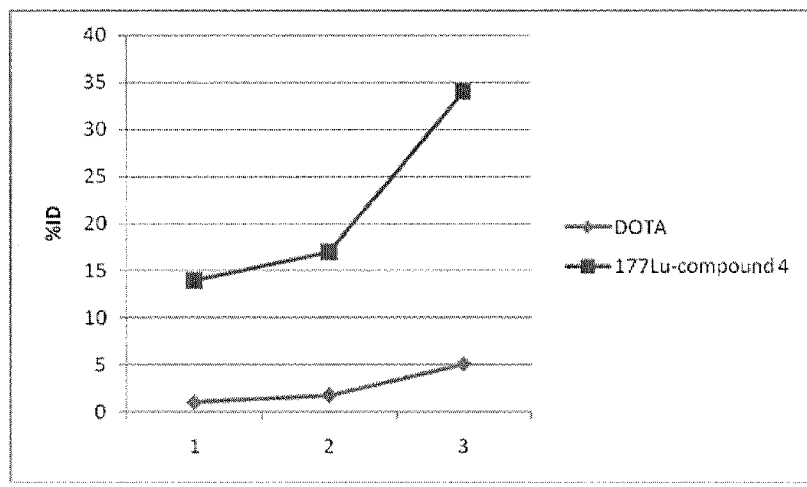
FIG. 27 illustrates cellular accumulation of $^{177}$Lu-4
Figure 28:
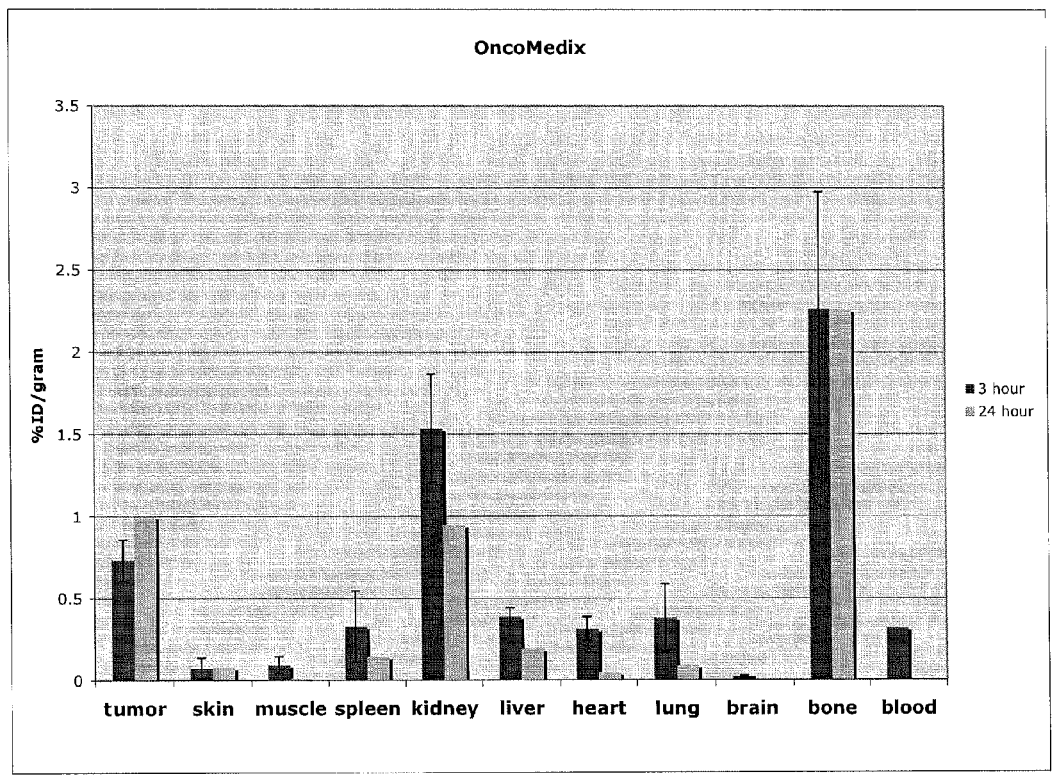
FIG. 28. Illustrates results of biodistribution study of $^{177}$Lu-4
Figure 29:
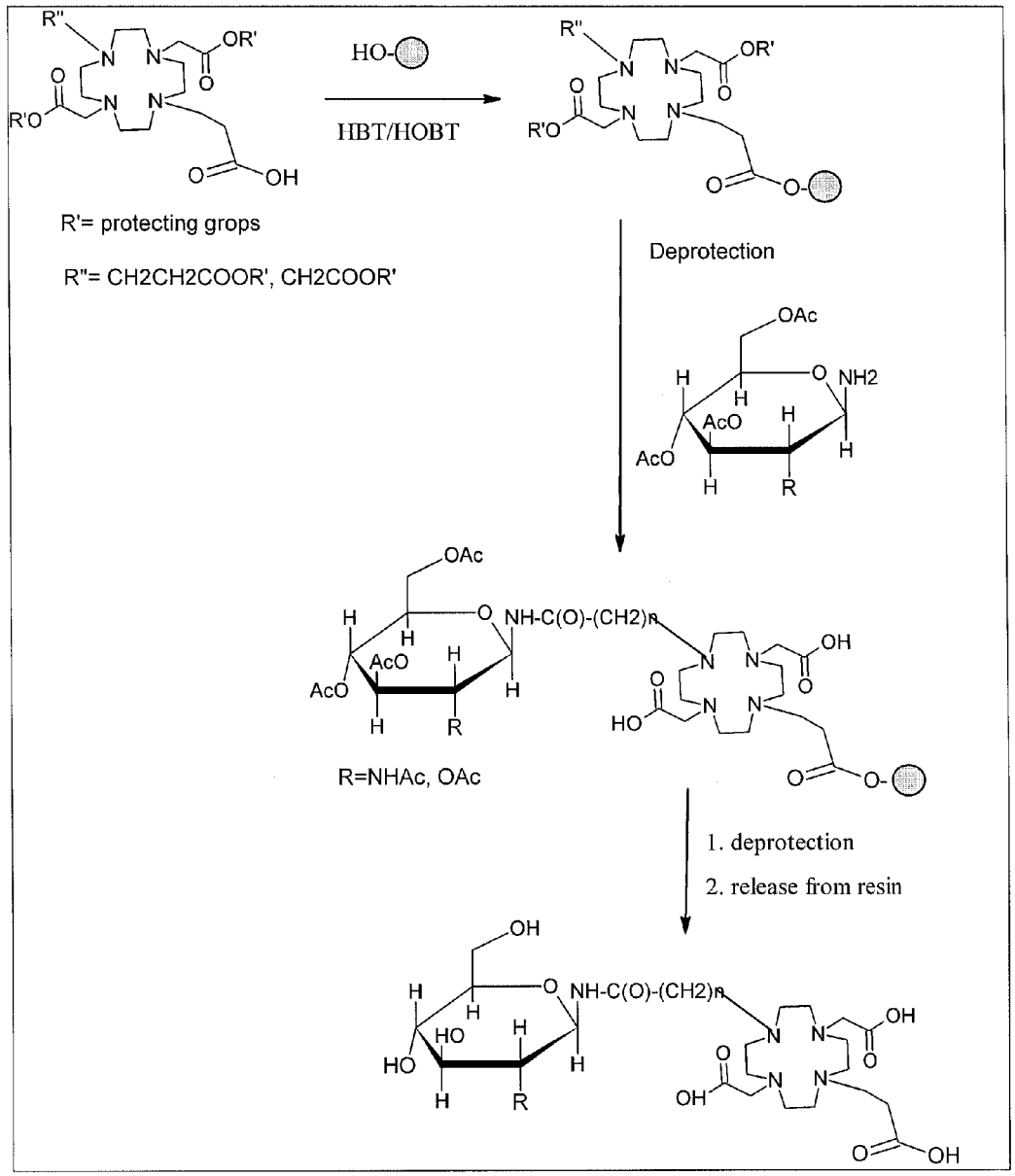
FIG. 29 illustrates general approach to the synthesis of DO2S-linker-carbohydrates.
Figure 30:
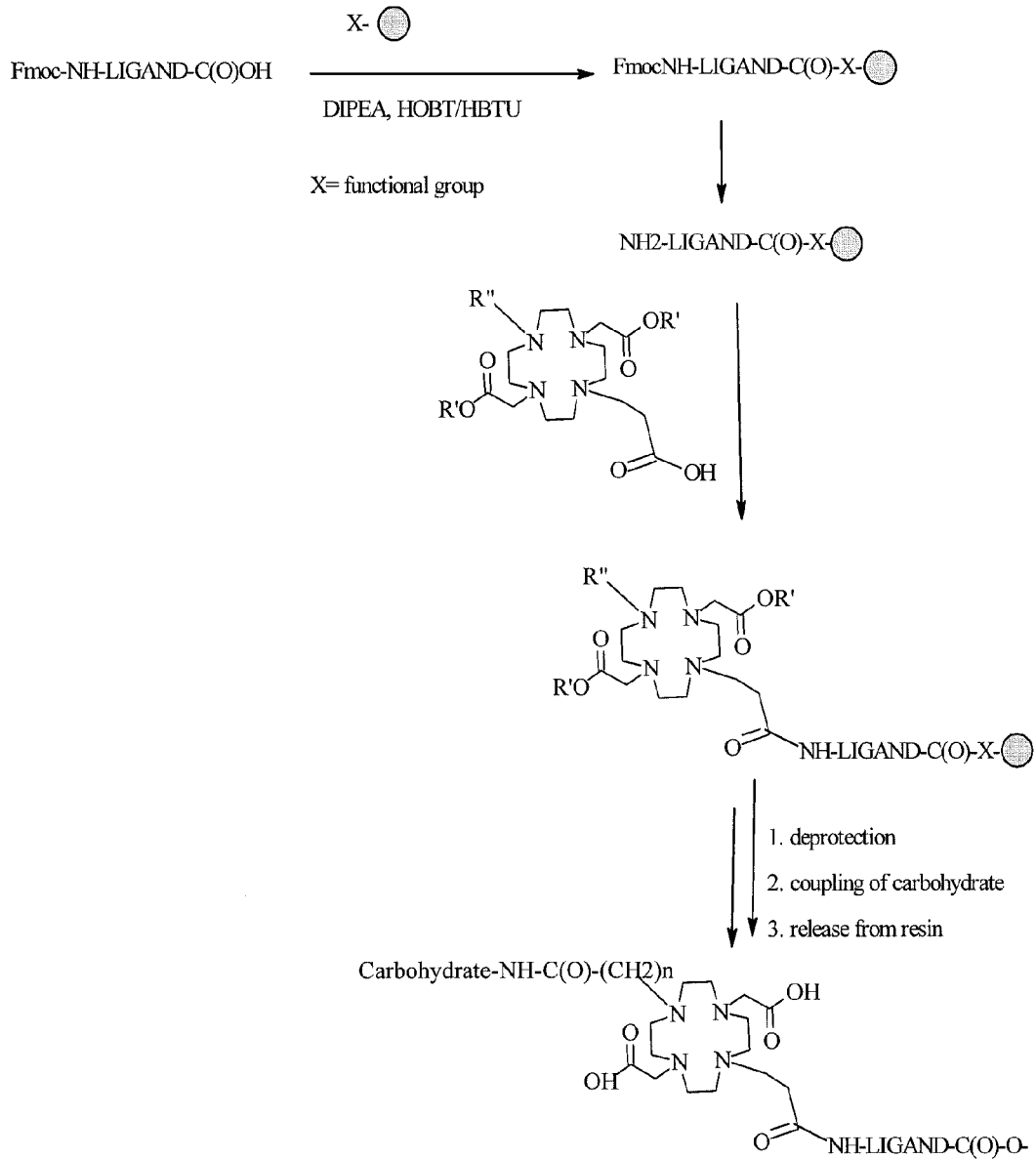
FIG. 30 illustrates an example of a method used for the synthesis of carbohydrate-DO2S-linker-carbohydrate by SPPS.
Figure 31:
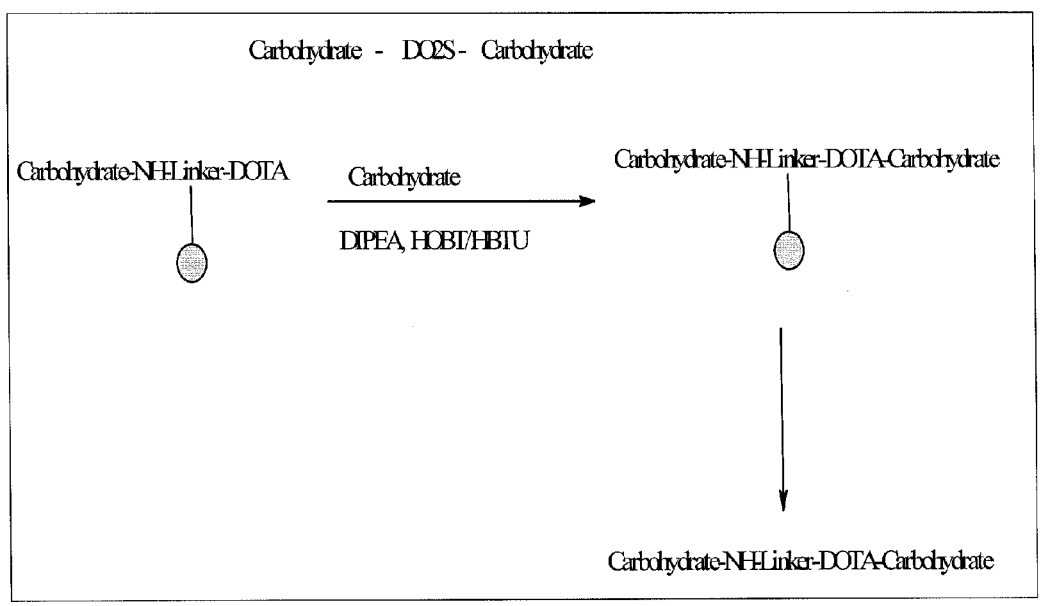
FIG. 31. illustrates an example of method used for the synthesis of di-substituted DO2S-[carbohydrate]2 by SPPS.
Figure 32:
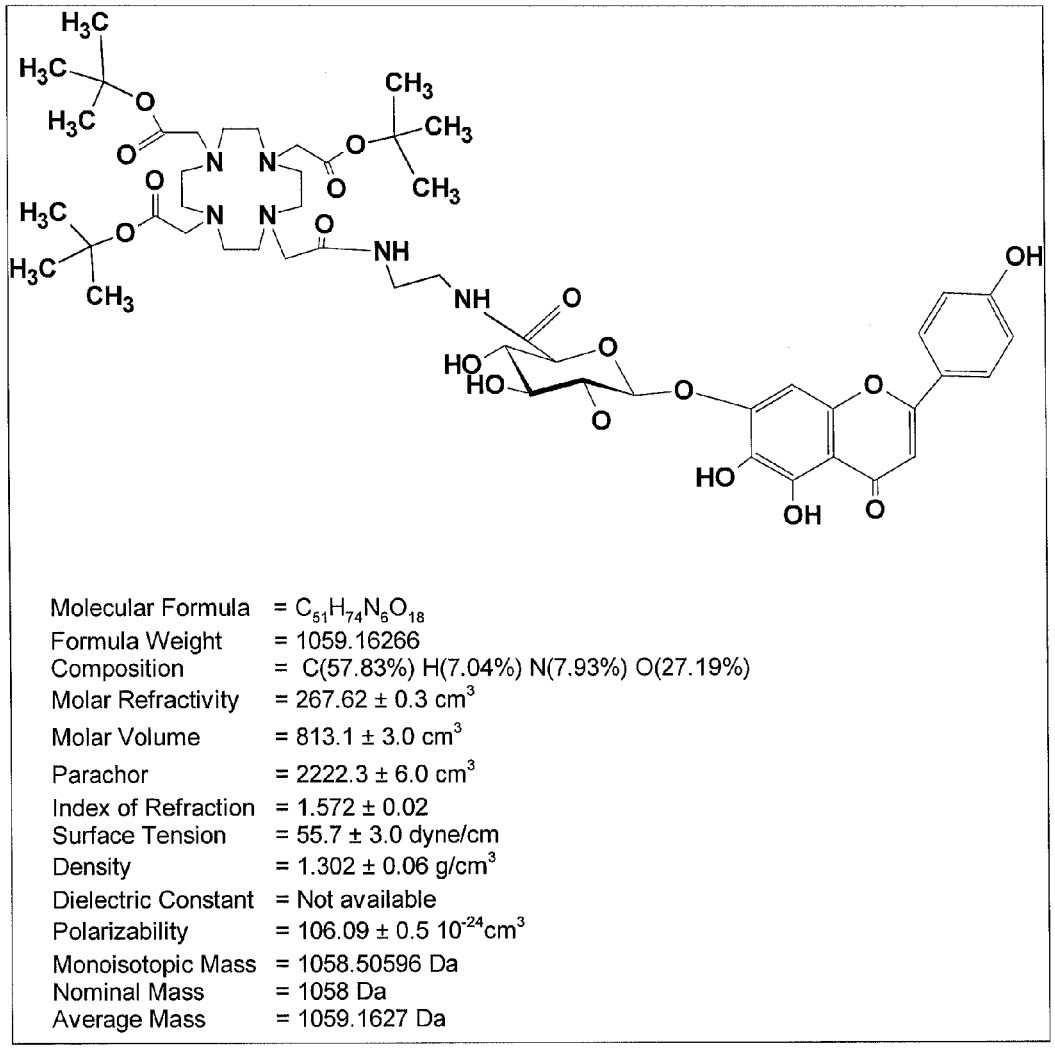
FIG. 32. illustrates structure of compound 5 and predicted physicochemical properties FIG. 33. illustrates the ESI-MS spectra of the t-Bu ester protected compound 5 purified by HPLC (C18 column)
Figure 33:
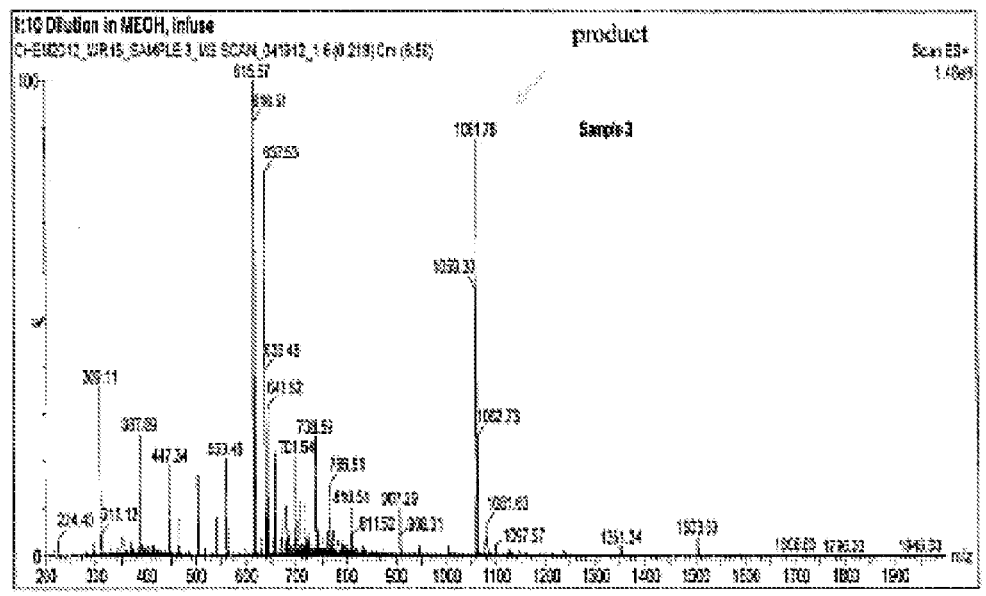
Figure 34:
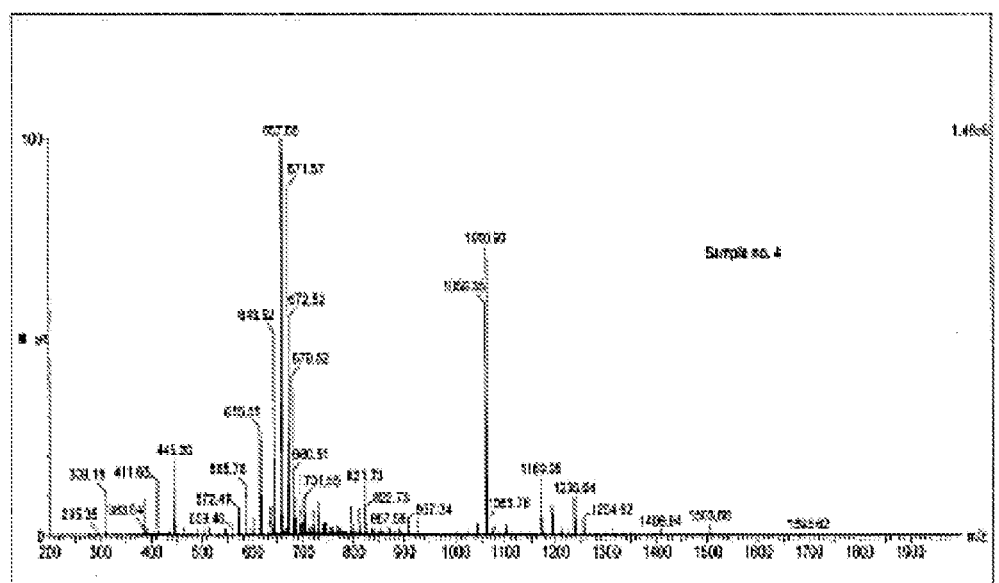
FIG. 34. illustrates the ESI-MS spectra of the t-Bu ester protected compound 5 after purification (precipitation with Et2O) and collecting of supernatant.
Figure 35:
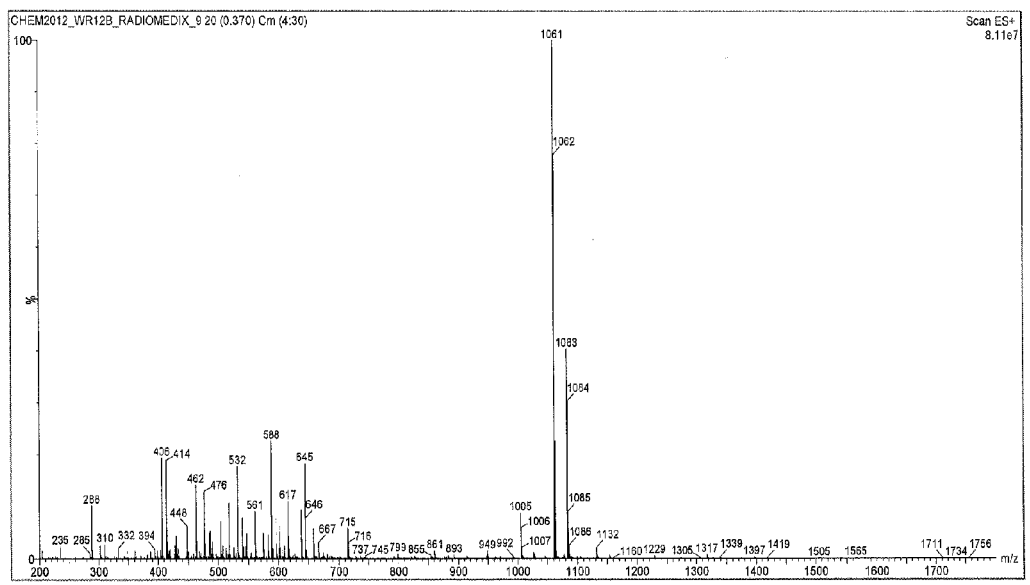
FIG. 35. illustrates the ESI-MS spectra of the t-Bu ester protected compound 5 after purification (precipitation with Et2O) and collecting of pellet.
Figure 36:
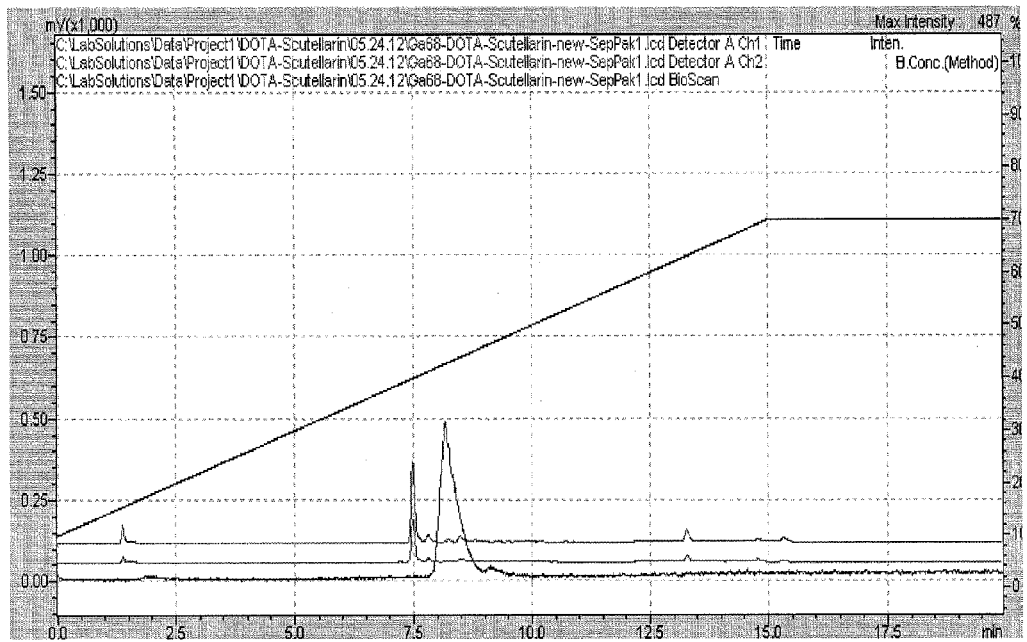
FIG. 36. illustrates radio-HPLC chromatogram (UV/Vis detection: 220 nm 275 nm) of the deprotected compound 5.
Figure 37:
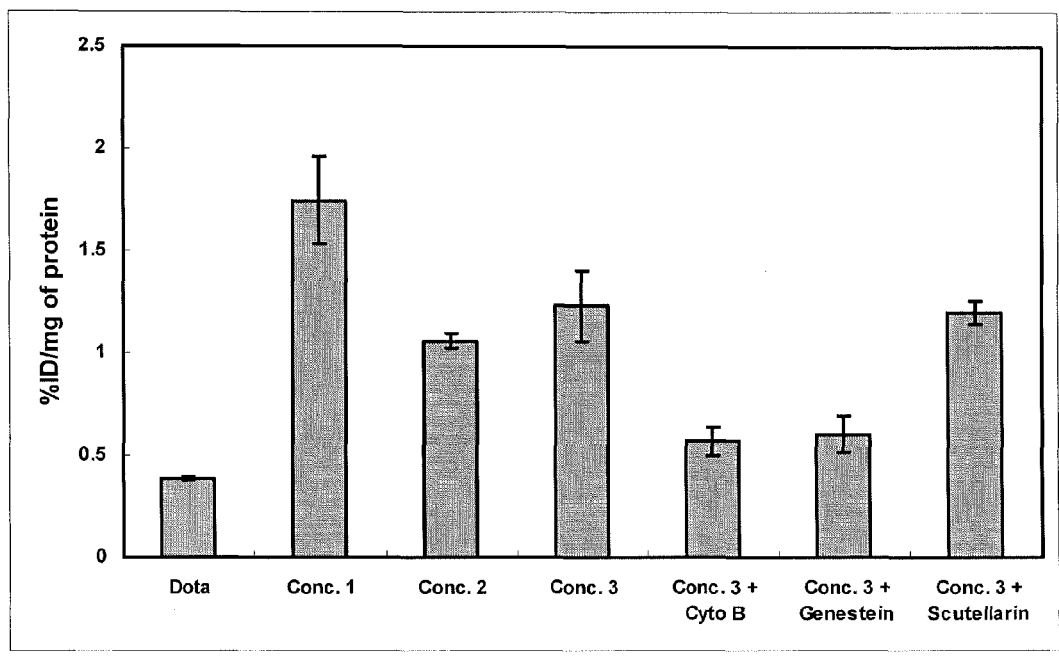
FIG. 37. illustrates cellular accumulation of 68Ga-5 in SKBr3 breast cancer cell line and results of blocking studies using cold GLUT-1 competitors (genistein, scutellarin, cytochalasin B).
Figure 38:
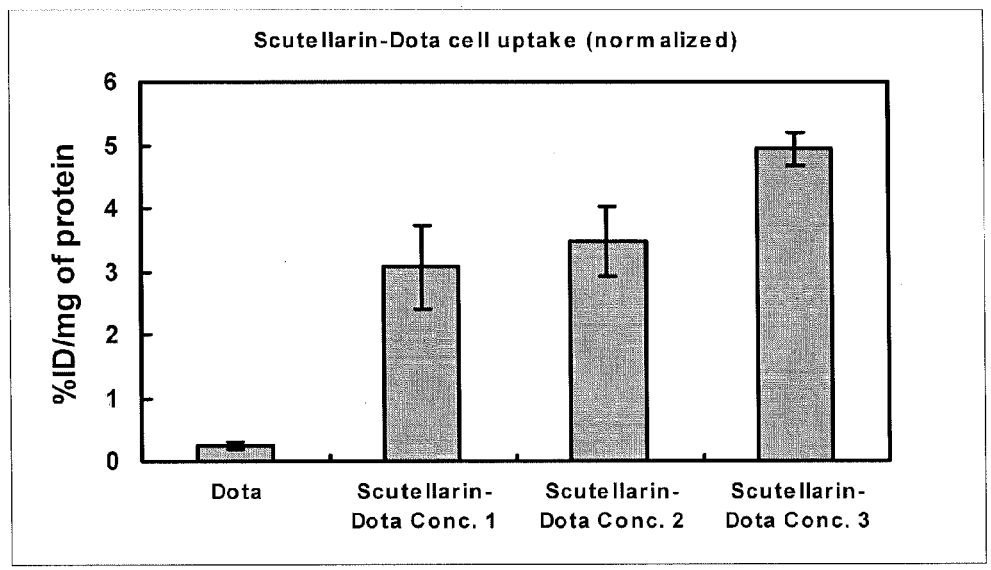
FIG. 38. illustrates concentration dependent accumulation studies of 68Ga-5 in SKBr3 breast cancer cell line.
Figure 39:
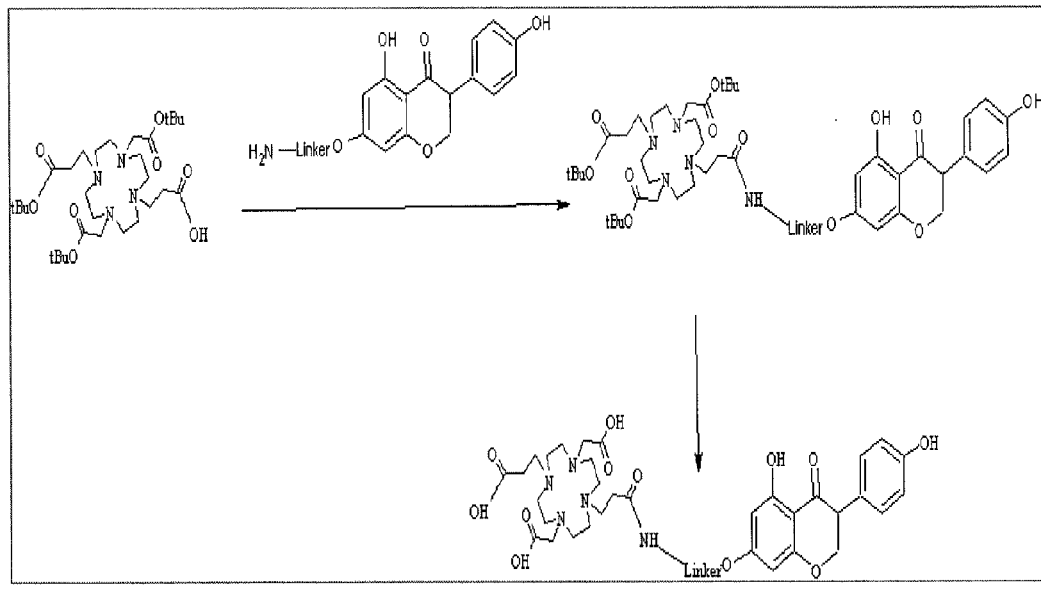
FIG. 39. illustrates an example of method used for the synthesis of DO2S-linker-[carbohydrate]-genistein compound 6
Figure 40:
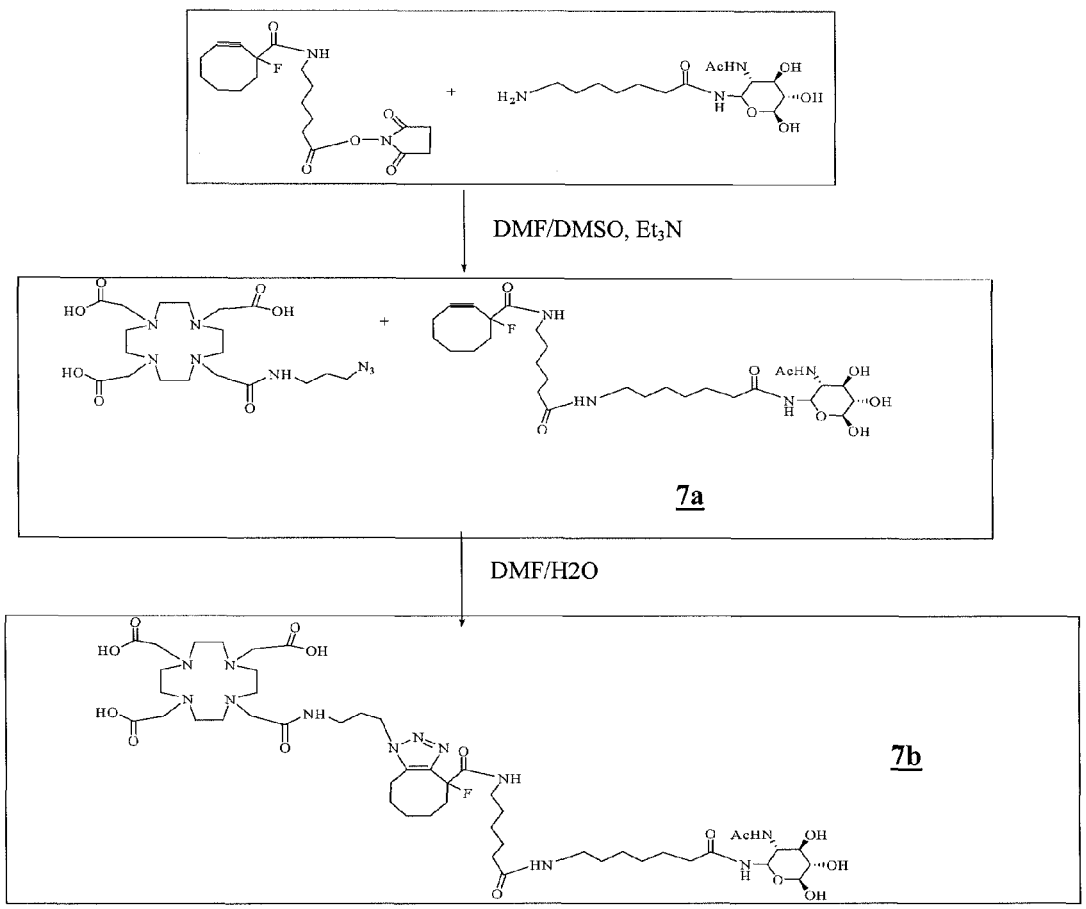
FIG. 40. illustrates an example of method used for the synthesis of DO2S-linker-[carbohydrate]-compound 7a,b.
Figure 41:
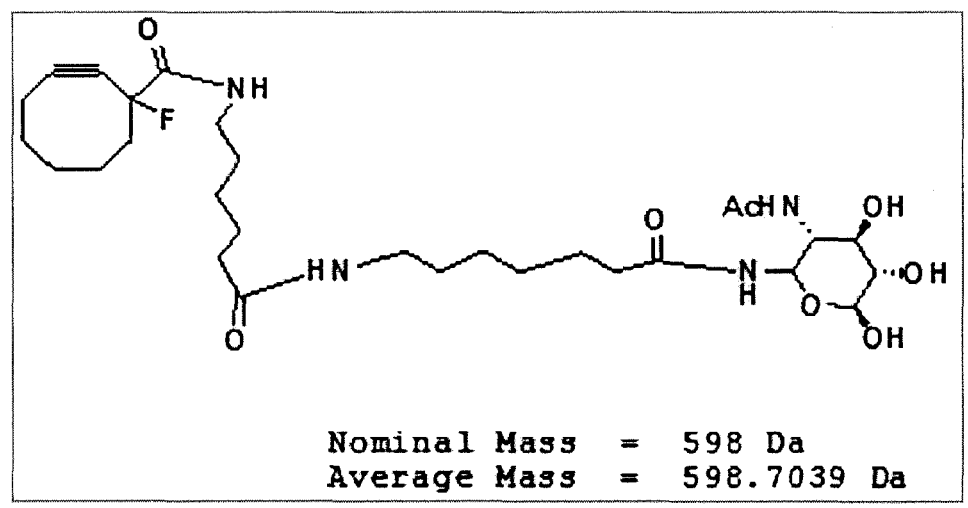
Figure 42:
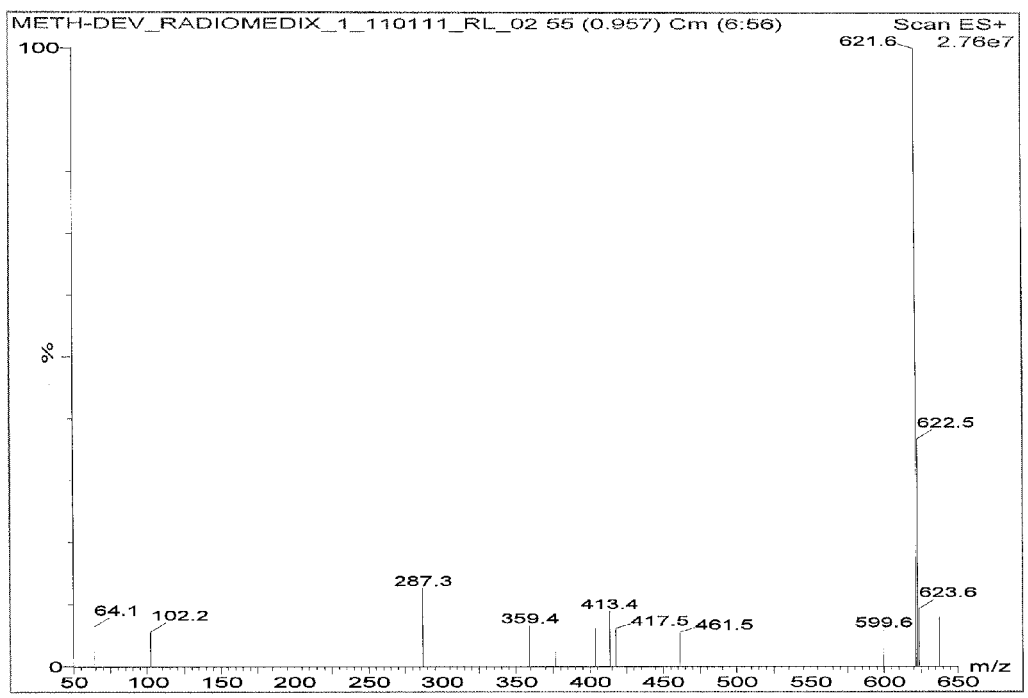
Figure 43:
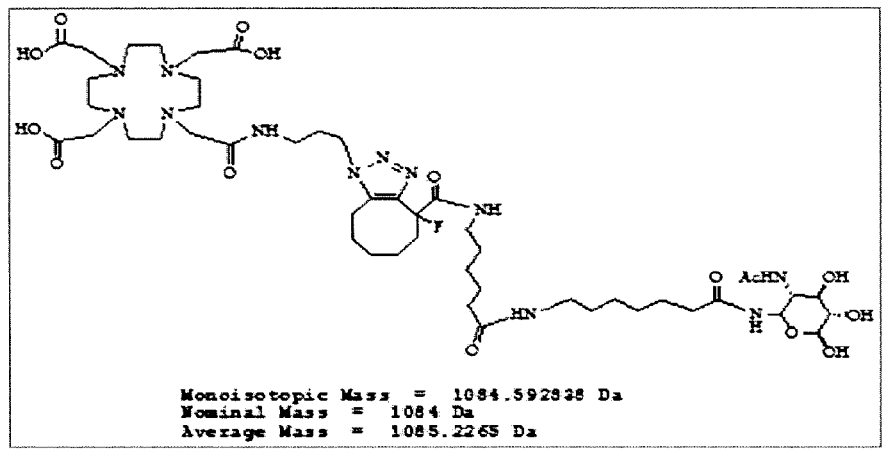
FIG. 43. illustrates structure of compound 7b
Figure 44:
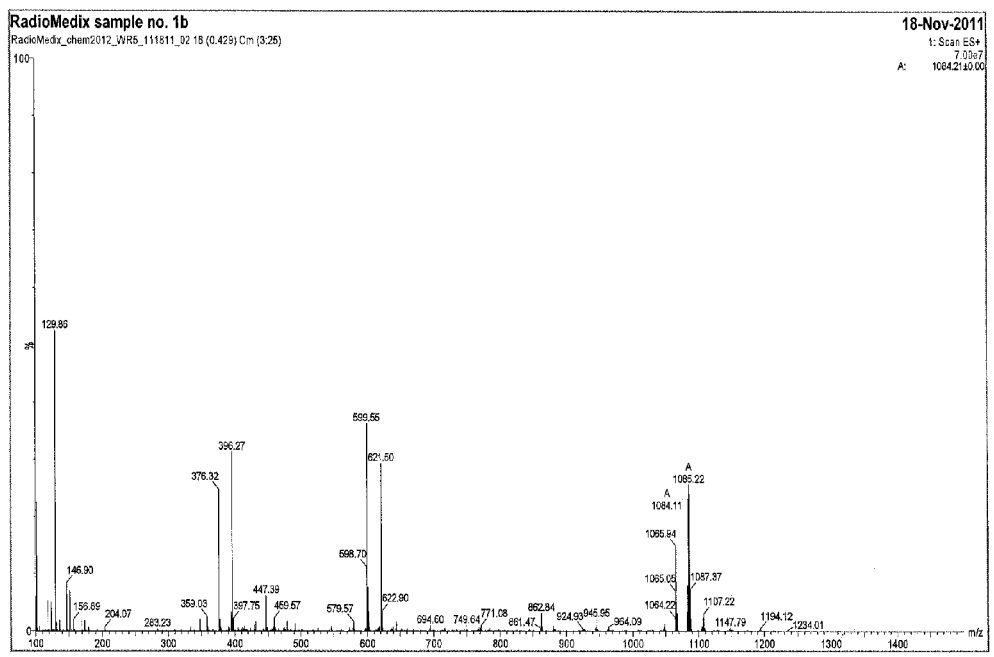
FIG. 44. illustrates the ESI-MS spectra of the compound 7b.
Figure 45:
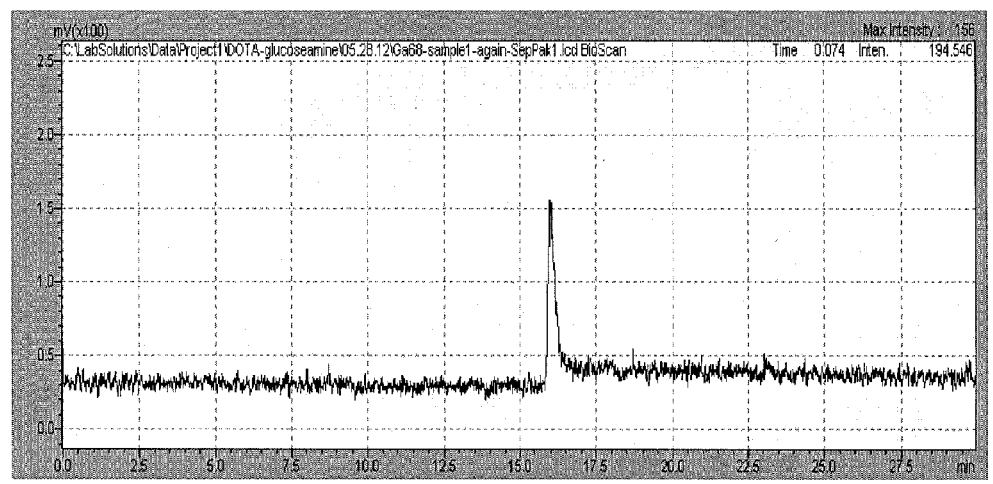
FIG. 45. illustrates radio-HPLC chromatogram of compound 7b.
Figure 46:
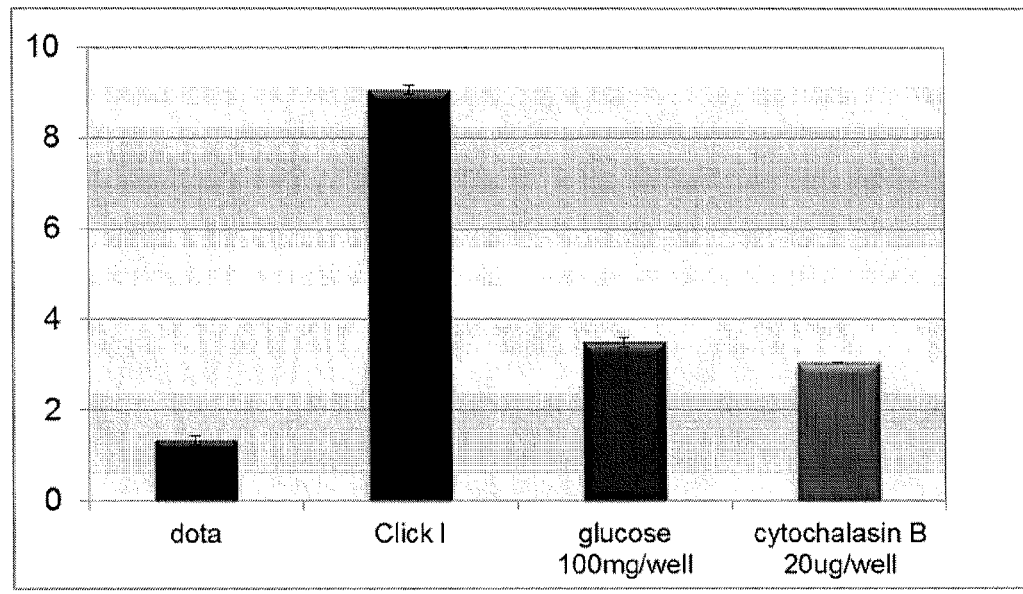
FIG. 46. illustrates cellular accumulation of $^{68}$Ga-7b in SKBr3 breast cancer cell line. Specificity of binding was confirmed in blocking studies using cold GLUT-1 competitors (glucose, cytochalasin B).
Figure 47:
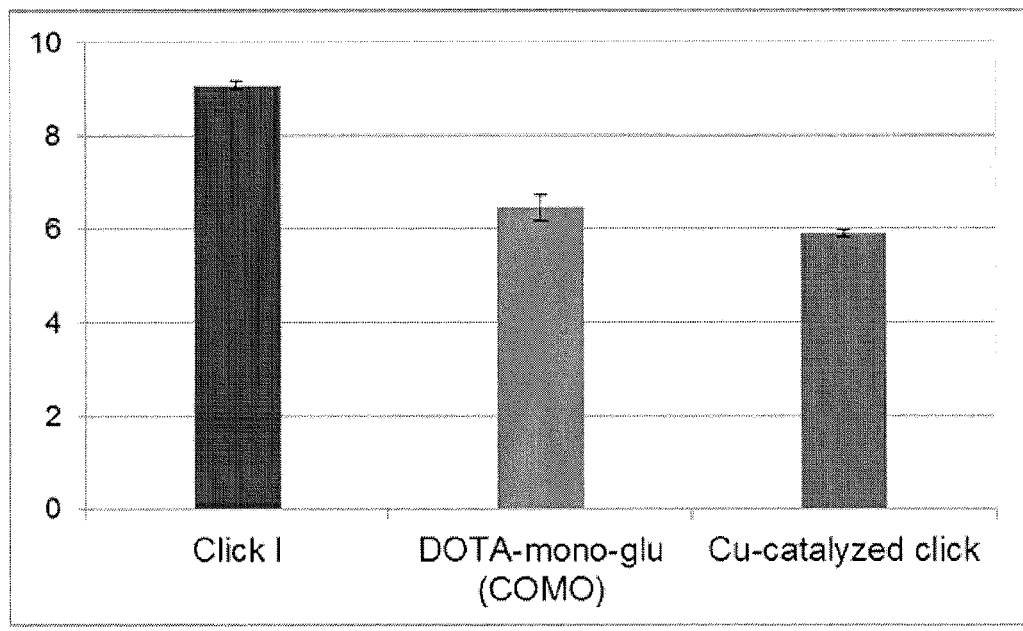
FIG. 47. illustrates cellular accumulation of $^{68}$Ga-7b, $^{68}$Ga-1 and $^{68}$Ga-copper catalyzed glucosamine conjugate in SKBr3 breast cancer cell line.

Step 3. Synthesis of N-1-(ε-aminocaproyl)-β-N-acetyl-2-deoxyglucopyranosyl N-[1,4,7,10-Tetraazacyclododecane-1,4,7,10-tetra-(acetyl acid)] (FIG. 23). DOTA conjugate (6) was dissolved in DMSO (1 ml), Et3N (0.3 ml) and coupling agent HATU were added to the solution. The mixture was allowed to preactivate for approx 30 min. In a separate vial N(ε-aminocaproyl)-N-acetylglucosaminylamine (5) was dissolved in DMSO and added to the preactivated DOTA solution. The mixture was allowed to react at rt with constant stirring for 24 h. The reaction mixture was then concentrated under reduced pressure and purified by flash chromatography. Deprotection of tbu ester groups will be performed by addition of TFA (0.5 ml)/DCM (0.5 ml) to the DOTA ester at 0° C. Then the reaction was stirred for 3 h. The solvent was then removed under reduced pressure, precipitated with anhydrous diethyl ether and dried under high vacuum.

E.2. 68Ga-labeling of compound 4. Radiolabeling was performed in 0.5M NaOAc pH=4.4 at 700 C for 20 min iTLC was developed in standard running buffer (0.5M NH4OAC:methanol 1:1 v/v). Radio-TLC (Bioscan) analysis showed the radiochemical purity of tracer was >99%.

E.3. Cellular accumulation of 68Ga-4. A549 and SKBr3 cells were plated in 12 well plates at a density of 2*10^5 cells per well and grown overnight in DMEM containing 5.4 mg/ml glucose and 10% FBS at 37° C., 5% CO2. Cells were fasted for 30 min prior to the study with glucose free DMEM. At the start of the study, media was removed from each well and replaced with 0.5 ml glucose free DMEM (Cellgro) containing 0.5-1⌴Ci 68Ga-4 or 68Ga DOTA. Cells were incubated at 37° C., 5% CO2 for the indicated time. The radioactive media was then removed and cells were washed twice with 1 ml PBS. Cells were then trypsinized and transferred to counting tubes. Radioactivity in cells and media were counted at 511 keV using a Perkin Elmer Wizard gamma counter. Cells were then collected and lysed with RIPA buffer (Invitrogen) and protein concentration was determined by Pierce BCA protein assay kit (ThermoFisher). Data is expressed as % ID (cpm cells/cpm media*100)/mg protein. Error bars represent Standard deviation. Black lines represent linear regression analysis. Studies were preformed in triplicate.

E.4. Cellular accumulation of 177Lu-4. A549 cells were plated in 12 well plates at a density of 2*10^5 cells per well and grown overnight in DMEM containing 5.4 mg/ml glucose and 10% FBS at 37° C., 5% CO2. Cells were fasted for 30 min prior to the study with glucose free DMEM. At the start of the study, media was removed from each well and replaced with 0.5 ml glucose free DMEM (Cellgro) containing 0.5 microCi 177Lu-4 or 177Lu-DOTA. Cells were incubated at 37° C., 5% CO2 for the indicated time. The radioactive media was then removed and cells were washed twice with 1 ml PBS. Cells were then trypsinized and radioactivity was counted. Data is presented as % cpm cells/cpm media E.5. Biodistribution study of 177Lu-4. Tumor xenografts were generated in 6 week old Swiss nu/nu mice using the human lung adenocarcinoma cell line A549. Xenografts were generated by subcutaneous inoculation of 2*10^6 cells per mouse into the right shoulder. Xenografts were allowed to grow for 7 days. Mice were fasted for 8-12 hours prior to the start of the study. On the day of the study, mice were anesthetized with Isofluorane and a tail vein cannula was inserted. The tracer was delivered via tail vein injection. Mice were placed on a warming pad or under a warming lamp to maintain body temperature. Mice were sacrificed at the indicated timepoints and organs were removed, weighed and counted. Data is expressed as % injected dose/gram tissue.

Example 6

F.1. Synthesis of Compound 5

To activate the carboxyl groups, carbohydrate-genistein (1 eq., 20 ug) was dissolved in 0.5 mL dimethylformamide DMF and dimethylsulfoxide DMSO and N-hydroxybenzotriazole (HOBT) and O-Benzotriazole-N,N,N',N'-tetramethyl-uronium-hexafluoro-phosphate (HBTU) coupling agents (1.5eq. each) were added in the presence of 4eq. of N,N-diisopropylamine (DIPEA). Reaction was left at room temperature for 30 min.

Step b. Coupling of DOTA-Linker-NH2 to Activated Carbohydrate-Genistein Derivative Pre-activated carbohydrate-genistein (1.5eq) was dissolved in DMF in the presence of DIPEA (4eq) and added to the solution DOTA-linker-NH2. Reaction was left stirring for 48 h at room temperature and was traced by TLC (chloroform:methanol 1:10) visualized using anisidine solution or dichlorofluoresceine. After completion of reaction, solution was evaporated and purified on HPLC (C18 column). The tert-butyl ester protecting groups were removed in the presence of 30% TFA:$CH_2Cl_2$:$H_2O$:TIS (950:250:250) and product was purified again by HPLC.

Alternatively, protected compound 5 was purified by precipitation using $Et_2O$ and fraction of supernatant was collected. The tert-butyl ester protecting groups were removed in the presence of 30% TFA:$CH_2Cl_2$:$H_2O$:TIS (950:250:250) and product was purified again by precipitation with $Et_2O$.

F.2. $^{68}$Ga-Radiolabeling of Compound 5

Compound 5 (1-10 ug) dissolved in 100 ul of 0.5M NaOAc buffer (pH=4.4). 0.5-4 mCi of $^{68}$GaCl$_3$ was added (eluted from the ITG $^{68}$Ge/$^{68}$Ga generator using 0.05M HCl). The final pH of the reaction was 4.1-4.4. The reaction mixture was heated at 95 C for 20 min After cooling to room temperature reaction was analyzed by radio-TLC.

F.3. In Vitro Evaluation of $^{68}$Ga-Compound 5 a) Cellular uptake study of $^{68}$Ga-compound 7. A549 cells were plated in 12 well plates at a density of 1.5*10^5 cells per well and grown overnight in DMEM containing 5.4 mg/ml glucose and 10% FBS at 37° C., 5% CO2. Cells were fasted for 30 min prior to the study with glucose free DMEM. At the start of the study, media was removed from each well and replaced with 0.5 ml glucose free DMEM (Cellgro) containing 12 uCi of $^{68}$Ga-5/ml or $^{68}$Ga DOTA or DMEM media containing 10 mmD-glucose and 12 uCi/ml of $^{68}$GA-5. Cells were incubated at 37° C., 5% CO2 for the indicated time. The radioactive media was then removed and cells were washed twice with 1 ml PBS. Cells were then trypsinized and radioactivity was counted. Data is expressed as % ID (cpm cells/cpm media*100). Error bars represent Standard deviation.

F.4. Cellular Accumulation and Blocking of $^{68}$Ga-5

SKBr3 cells were plated in 12 well plates at a density of 1.5*10^5 cells per well and grown overnight in DMEM containing 5.4 mg/ml glucose and 10% FBS at 37° C., 5% CO2. Cells were fasted for 20 min prior to the study with glucose free DMEM. At the start of the study, media was removed from each well and replaced with 0.5 ml glucose free DMEM (Cellgro) or media that contained 100 mg/ml D or L glucose (Sigma alrich) and 12 uCi/ml of radiolabeled compound. Cells were incubated at 37° C., 5% CO2 for 1 hour. The radioactive media was then removed and cells were washed twice with 1 ml PBS. Cells were then trypsinized and transferred to counting tubes. Radioactivity in cells and media were counted at 511 keV using a Perkin Elmer Wizard gamma counter. Cells were then collected and lysed with RIPA buffer (Invitrogen) and protein concentration was determined by Pierce BCA protein assay kit (ThermoFisher). Data is expressed as % ID (cpm cells/cpm media*100)/mg protein. Error bars represent Standard deviation. Data represents the average of four separate studies performed in triplicate.

F.4. Blocking of accumulation of $^{68}$Ga-5 by glucose transporter inhibitors. SKBr3 cells were plated in 12 well plates at a density of 1.5*10^5 cells per well and grown overnight in DMEM containing glucose transporters inhibitors (scutellarin, glucose, genistein, cytochalasin B) and 10% FBS at 37° C., 5% CO2. Cells were fasted for 20 min prior to the study with glucose free DMEM. At the start of the study, media was removed from each well and replaced with 0.5 ml glucose free DMEM (Cellgro) or media that contained 100 mg/ml D or L glucose (Sigma alrich) and 12 uCi/ml of radiolabeled compound. Cells were incubated at 37° C., 5% CO2 for 1 hour. The radioactive media was then removed and cells were washed twice with 1 ml PBS. Cells were then trypsinized and transferred to counting tubes.

Radioactivity in cells and media were counted at 511 keV using a Perkin Elmer Wizard gamma counter. Cells were then collected and lysed with RIPA buffer (Invitrogen) and protein concentration was determined by Pierce BCA protein assay kit (ThermoFisher). Data is expressed as % ID (cpm cells/cpm media*100)/mg protein. Error bars represent Standard deviation. Data represents the average of four separate studies performed in triplicate.

Example 7

G.1. Synthesis of Compound 6

To activate the carboxyl groups, tris-tBu ester DOTA (1 eq., 20 ug) was dissolved in 0.5 mL dimethylformamide DMF and dimethylsulfoxide DMSO and N-hydroxybenzotriazole (HOBT) and O-Benzotriazole-N,N,N',N'-tetramethyl-uronium-hexafluoro-phosphate (HBTU) coupling agents (1.5eq. each) were added in the presence of 4eq. of N,N-diisopropylamine (DIPEA). Reaction was left at room temperature for 30 min.

Step b. Coupling of Linker-Genistein to Activated DOTA-tris-tBu Ester

Pre-activated DOTAtris-tBuester (1.5eq) was dissolved in DMF in the presence of DIPEA (4eq) and combined with solution of genistein-linker-NH2. Reaction was left stirring for 48 h at room temperature and was traced by TLC (chloroform:methanol 1:10) visualized using anisidine solution or dichlorofluoresceine. After completion of reaction, solution was evaporated and purified on rHPLC (C18). The tert-butyl ester protecting groups were removed in the presence of 30% TFA:CH$_2$Cl$_2$:H$_2$O:TIS (950:250:250) and product was purified again by HPLC.

G.2. $^{68}$Ga-Radiolabeling of Compound 6

Compound 6 (1-10 ug) dissolved in 100 ul of 0.5M NaOAc buffer (pH=4.4). 0.5-4 mCi of $^{68}$GaCl$_3$ was added (eluted from the ITG $^{68}$Ge/$^{68}$Ga generator using 0.05M HCl). The final pH of the reaction was 4.1-4.4. The reaction mixture was heated at 95 C for 20 min. After cooling to room temperature reaction was analyzed by radio-TLC.

G.3. In Vitro Evaluation of $^{68}$Ga-Compound 6 a) Cellular uptake study of $^{68}$Ga-compound 6.A549 cells were plated in 12 well plates at a density of 1.5*10^5 cells per well and grown overnight in DMEM containing 5.4 mg/ml glucose and 10% FBS at 37° C., 5% CO2. Cells were fasted for 30 min prior to the study with glucose free DMEM. At the start of the study, media was removed from each well and replaced with 0.5 ml glucose free DMEM (Cellgro) containing 12 uCi of $^{68}$Ga-6/ml or $^{68}$Ga DOTA or DMEM media containing 10 mmD-glucose and 12 uCi/ml of $^{68}$GA-6. Cells were incubated at 37° C., 5% CO2 for the indicated time. The radioactive media was then removed and cells were washed twice with 1 ml PBS. Cells were then trypsinized and radioactivity was counted. Data is expressed as % ID (cpm cells/cpm media*100). Error bars represent Standard deviation.

G.4 Cellular Accumulation and Blocking of $^{68}$Ga-6

SKBr3 cells were plated in 12 well plates at a density of 1.5*10^5 cells per well and grown overnight in DMEM containing 5.4 mg/ml glucose and 10% FBS at 37° C., 5% CO2. Cells were fasted for 20 min prior to the study with glucose free DMEM. At the start of the study, media was removed from each well and replaced with 0.5 ml glucose free DMEM (Cellgro) or media that contained 100 mg/ml D or L glucose (Sigma alrich) and 12 uCi/ml of radiolabeled compound. Cells were incubated at 37° C., 5% CO2 for 1 hour. The radioactive media was then removed and cells were washed twice with 1 ml PBS. Cells were then trypsinized and transferred to counting tubes. Radioactivity in cells and media were counted at 511 keV using a Perkin Elmer Wizard gamma counter. Cells were then collected and lysed with RIPA buffer (Invitrogen) and protein concentration was determined by Pierce BCA protein assay kit (ThermoFisher). Data is expressed as % ID (cpm cells/cpm media*100)/mg protein. Error bars represent Standard deviation. Data represents the average of four separate studies performed in triplicate.

G.5. Blocking of accumulation of $^{68}$Ga-6 by glucose transporter inhibitors. SKBr3 cells were plated in 12 well plates at a density of 1.5*10^5 cells per well and grown overnight in DMEM containing glucose and 10% FBS at 37° C., 5% CO2. Cells were fasted for 20 min prior to the study with glucose free DMEM. At the start of the study, media was removed from each well and replaced with 0.5 ml DMEM (Cellgro) containing GLUT-1 inhibitors (scutellarin, glucose, genistein, cytochalasin B) and 12 uCi/ml of radiolabeled compound. Cells were incubated at 37° C., 5% CO2 for 1 hour. The radioactive media was then removed and cells were washed twice with 1 ml PBS. Cells were then trypsinized and transferred to counting tubes. Radioactivity in cells and media were counted at 511 keV using a Perkin Elmer Wizard gamma counter. Cells were then collected and lysed with RIPA buffer (Invitrogen) and protein concentration was determined by Pierce BCA protein assay kit (ThermoFisher). Data is expressed as % ID (cpm cells/cpm media*100)/mg protein. Error bars represent Standard deviation. Data represents the average of four separate studies performed in triplicate.

Example 8

H.1. Synthesis of Compound 7

Step.a. Synthesis of Compound 7a 2-acetamido-N-(ε-minocaproyl)-2-deoxy-β-D-glucosylamine (1eq., 30 ug) was dissolved in 0.5 mL dimethylformamide DMF and dimethylsulfoxide DMF/H2O and were added to MFCO-NHS dissolved in DMF/H2O. Reaction was left at room temperature for 24 h.

Step b. Synthesis of Compound 7b

Compound 7a (1.5eq) and DOTA-linker-N3(10eq) were dissolved in DMF/H2O and reaction was left stirring for 48 h at room temperature. Progress of reaction was monitored by TLC (chloroform:methanol 1:10) visualized using anisidine solution or dichlorofluoresceine. Final product was purified by rHPLC.

H.2. $^{68}$Ga-Radiolabeling of Compound 7b

Compound 7b (1-10 ug) dissolved in 100 ul of 0.5M NaOAc buffer (pH=4.4). 0.5-4 mCi of $^{68}$GaCl$_3$ was added (eluted from the ITG $^{68}$Ge/$^{68}$Ga generator using 0.05M HCl). The final pH of the reaction was 4.1-4.4. The reaction mixture was heated at 95 C for 20 min. After cooling to room temperature reaction was analyzed by radio-TLC.

H.3. In Vitro Evaluation of $^{68}$Ga-Compound 7b a) Cellular uptake study of $^{68}$Ga-compound 7b. A549 cells were plated in 12 well plates at a density of 1.5*10^5 cells per well and grown overnight in DMEM containing 5.4 mg/ml glucose and 10% FBS at 37° C., 5% CO2. Cells were fasted for 30 min prior to the study with glucose free DMEM. At the start of the study, media was removed from each well and replaced with 0.5 ml glucose free DMEM (Cellgro) containing 12 uCi of $^{68}$Ga-7b/ml or $^{68}$Ga DOTA or DMEM media containing 10 mmD-glucose and 12 uCi/ml of $^{68}$GA-7b. Cells were incubated at 37° C., 5% CO2 for the indicated time. The radioactive media was then removed and cells were washed twice with 1 ml PBS. Cells were then trypsinized and radioactivity was counted. Data is expressed as % ID (cpm cells/cpm media*100). Error bars represent Standard deviation.

H.4 Cellular Accumulation and Blocking of $^{68}$Ga-7b

SKBr3 cells were plated in 12 well plates at a density of 1.5*10^5 cells per well and grown overnight in DMEM containing 5.4 mg/ml glucose and 10% FBS at 37° C., 5% CO2. Cells were fasted for 20 min prior to the study with glucose free DMEM. At the start of the study, media was removed from each well and replaced with 0.5 ml glucose free DMEM (Cellgro) or media that contained 100 mg/ml D or L glucose (Sigma Alrich) and 12 uCi/ml of radiolabeled compound. Cells were incubated at 37° C., 5% CO2 for 1 hour. The radioactive media was then removed and cells were washed twice with 1 ml PBS. Cells were then trypsinized and transferred to counting tubes. Radioactivity in cells and media were counted at 511 keV using a Perkin Elmer Wizard gamma counter. Cells were then collected and lysed with RIPA buffer (Invitrogen) and protein concentration was determined by Pierce BCA protein assay kit (ThermoFisher). Data is expressed as % ID (cpm cells/cpm media*100)/mg protein. Error bars represent Standard deviation. Data represents the average of four separate studies performed in triplicate.

H.5. Blocking of Accumulation of $^{68}$Ga-7b by Glucose Transporter Inhibitors

SKBr3 cells were plated in 12 well plates at a density of 1.5*10^5 cells per well and grown overnight in DMEM containing glucose and 10% FBS at 37° C., 5% CO2. Cells were fasted for 20 min prior to the study with glucose free DMEM. At the start of the study, media was removed from each well and replaced with 0.5 ml glucose free DMEM (Cellgro) or media that contained 100 mg/ml D or L glucose (Sigma alrich) or other GLUT1 inhibitors (genistein, scutellarin, cytochalasin B) and 12 uCi/ml of radiolabeled compound. Cells were incubated at 37° C., 5% CO2 for 1 hour. The radioactive media was then removed and cells were washed twice with 1 ml PBS. Cells were then trypsinized and transferred to counting tubes. Radioactivity in cells and media were counted at 511 keV using a Perkin Elmer Wizard gamma counter. Cells were then collected and lysed with RIPA buffer (Invitrogen) and protein concentration was determined by Pierce BCA protein assay kit (ThermoFisher). Data is expressed as % ID (cpm cells/cpm media*100)/mg protein. Error bars represent Standard deviation. Data represents the average of four separate studies performed in triplicate.

What is claimed is:
1. A composition comprising a DO2S derivative conjugated to a monosaccharide ligand directly or through a linker and optionally chelated to a metal, wherein the DO2S derivative has the following structure:

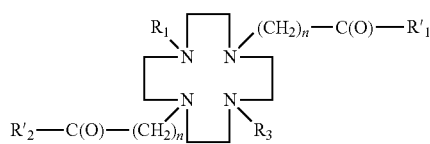

wherein R$_1$', and R$_2$' are each independently —OH; R$_1$, and R$_3$ comprise a ligand, optionally attached to the DO2S derivative via a linker; n is 1; the linker is an amino acid, a peptide, an amino alcohol, a polyethylene glycol, an alkyl, an alkenyl, an alkynyl, an azide, an aromatic compound, a carboxylic acid, or an ester, the alkyl, alkenyl, or alkynyl is optionally substituted with an alkyl, a halogen, a nitro group, a hydroxyl group, an amino group, or a carboxyl group; and the ligand is a GLUT1 targeting moiety, wherein the GLUT-1 targeting moiety is 2-deoxyglucose, a 1'2'-diaminosugar, genistein, and/or scutellarin.

2. The composition of claim 1, wherein the linker comprises —(CH2)$_m$—X, wherein X is a hydroxyl, an amino, or a carboxyl group, and m is an integer from 1 to 10, and wherein the linker may be optionally substituted with an alkyl, a halogen, a nitro group, a hydroxyl group, an amino group, or a carboxyl group.

3. The composition of claim 1, wherein the DO2S derivative further comprises a radiometal.

4. The composition of claim 3, wherein the radiometal is $^{68}$Ga or $^{177}$Lu.

5. A method for synthesizing a composition comprising a DO2S derivative conjugated to a monosaccharide ligand directly or through a linker and optionally chelated to a metal, wherein the DO2S derivative has the following structure:

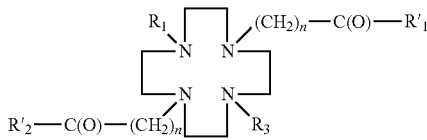

wherein R$_1$', and R$_2$' are each independently —OH; R$_1$, and R$_3$ comprise a ligand, optionally attached to the DO2S derivative via a linker; n is 1; the linker is an amino acid, a peptide, an amino alcohol, a polyethylene glycol, an alkyl, an alkenyl, an alkynyl, an azide, an aromatic compound, a carboxylic acid, or an ester, the alkyl, alkenyl, or alkynyl is optionally substituted with an alkyl, a halogen, a nitro group, a hydroxyl group, an amino group, or a carboxyl group; and the ligand is a GLUT1 targeting moiety comprising a 2-deoxyglucose, a 1'2'-diaminosugar, genistein, and/or scutellarin, the method comprising the following steps:

providing the ligand bound to a branch linker at a proximal end of the branch linker, a distal end of the branch linker having two different reactive group ends;

attaching a first free reactive group end of the branch linker to a solid support;

deprotecting a second reactive group end of the branch linker;

conjugating the deprotected second reactive group end of the branch linker to a chelator to form a chelator-linker ligand conjugate DO2S derivative, immobilized on the solid support;

deprotecting functional carboxyl groups on the chelator;

radiolabeling the DO2S derivative immobilized on the solid support with an isotope; and releasing the radiolabeled DO2S derivative from the solid support by cleavage of the branch linker from the solid support.

6. The composition of claim 1, wherein the DO2S derivative further comprises a paramagnetic substance, the paramagnetic substance selected from the group consisting of Gd, Mn, Cu, and Fe.

7. The composition of claim 3, wherein the radiometal is selected from the group consisting of a α-emitter, a β-emitter, a γ-emitter, and a β/γ-emitter.

8. The composition of claim 3, wherein the radiometal is selected from the group consisting of $^{45}$Ti, $^{59}$Fe, $^{60}$Cu, $^{61}$Cu, $^{62}$Cu, $^{64}$Cu, $^{67}$Cu, $^{67}$Ga, $^{89}$Sr, $^{90}$Y, $^{86}$Y, $^{94m}$Tc, $^{99m}$Tc, $^{111}$In, $^{149}$Pm, $^{153}$Gd, $^{153}$Sm, $^{166}$Ho, $^{186}$Re, $^{188}$Re, $^{211}$At, $^{212}$Bi, and $^{225}$Ac.

* * * * *